United States Patent
Barbour et al.

(10) Patent No.: US 11,396,542 B2
(45) Date of Patent: Jul. 26, 2022

(54) ASTROTACTIN1-BASED COMPOSITIONS AND PHARMACEUTICAL FORMULATIONS

(71) Applicants: SF17 THERAPEUTICS, INC., Oakland, CA (US); MACROMOLTEK, INC., Austin, TX (US)

(72) Inventors: Jason Barbour, Piedmont, CA (US); David Ott, San Francisco, CA (US); Monica Berrondo, Austin, TX (US); Susana Kaufmann, Austin, TX (US)

(73) Assignee: Synkrino Biotherapeutics, Inc., Oakland, CA (US)

( * ) Notice: Subject to any disclaimer, the term of this patent is extended or adjusted under 35 U.S.C. 154(b) by 0 days.

(21) Appl. No.: 16/772,150

(22) PCT Filed: Aug. 21, 2019

(86) PCT No.: PCT/US2019/047596
§ 371 (c)(1),
(2) Date: Jun. 11, 2020

(87) PCT Pub. No.: WO2020/041532
PCT Pub. Date: Feb. 27, 2020

(65) Prior Publication Data
US 2021/0246203 A1 Aug. 12, 2021

Related U.S. Application Data

(60) Provisional application No. 62/720,138, filed on Aug. 21, 2018.

(51) Int. Cl.
| | |
|---|---|
| *C07K 16/28* | (2006.01) |
| *A61K 39/395* | (2006.01) |
| *A61P 25/28* | (2006.01) |
| *A61K 45/06* | (2006.01) |
| *G01N 33/53* | (2006.01) |
| *C07K 14/705* | (2006.01) |
| *A61K 39/00* | (2006.01) |

(52) U.S. Cl.
CPC .......... *C07K 16/28* (2013.01); *A61K 39/3955* (2013.01); *A61K 45/06* (2013.01); *A61P 25/28* (2018.01); *G01N 33/53* (2013.01); *A61K 2039/505* (2013.01); *A61K 2039/54* (2013.01); *C07K 14/705* (2013.01); *C07K 2317/56* (2013.01); *C07K 2317/622* (2013.01); *G01N 2333/52* (2013.01); *G01N 2333/705* (2013.01); *G01N 2800/2835* (2013.01)

(58) Field of Classification Search
CPC ..... C07K 16/28; A61K 39/3955; A61P 25/28; G01N 2333/705
See application file for complete search history.

(56) References Cited

U.S. PATENT DOCUMENTS

2014/0271617 A1  9/2014  Igawa et al.

FOREIGN PATENT DOCUMENTS

| WO | 1997/040155 A1 | 10/1997 |
| WO | 2008/052187 A2 | 5/2008 |
| WO | 2013/046722 A1 | 4/2012 |
| WO | 2012/109285 A2 | 8/2012 |

OTHER PUBLICATIONS

McColgan et al, 2018. European Journal of Neurology. 25: 24-34.*
Chang et al, 2017. IUBMB Life. 69(8): 572-577.*
Miller et al, 2016 (Human Molecular Genetics. 25(14): 2893-2904).*
Miller et al, 2016, Supplementary Dataset S1; available at http://europepmc.org/article/PMC/5181590, 1 page as printed.*
International Search Report and Written Opinion in International Application No. PCT/US2019/047596, dated Jan. 10, 2020.

* cited by examiner

*Primary Examiner* — Zachary C Howard
(74) *Attorney, Agent, or Firm* — Cognition IP, P.C.; Edward Steakley

(57) ABSTRACT

Methods of detecting, preventing, treating, controlling or managing progressive neurodegenerative diseases are provided. These methods comprise the administration of antibodies that reduce or eliminate monocytes that abnormally express Astrotactin (ASTN1), or block blood monocytes that abnormally express ASTN1 from migrating to the central nervous system. Also provided are pharmaceutical compositions that comprise antibodies that specifically target the extracellular domain (ECD2) of ASTN1 for the prevention, treatment, control or management of progressive neurodegenerative diseases.

7 Claims, 11 Drawing Sheets
Specification includes a Sequence Listing.

Reducing SDS-PAGE confirmed low concentrations of ASTN1 variants

SEQUENCE LISTING

```
<160> NUMBER OF SEQ ID NOS: 16

<210> SEQ ID NO 1
<211> LENGTH: 122
<212> TYPE: PRT
<213> ORGANISM: Artificial Sequence
<220> FEATURE:
<223> OTHER INFORMATION: Heavy chain variable region

<400> SEQUENCE: 1

Glu Val Gln Leu Val Glu Ser Gly Gly Gly Leu Val Gln Pro Gly Gly
1               5                   10                  15
```

```
Ser Leu Arg Leu Ser Cys Ser Val Thr Gly Glu Pro Ile Thr Ser Gly
            20                  25                  30

Phe Trp Asp Trp Val Arg Gln Ala Thr Gly Lys Gly Leu Glu Phe Val
        35                  40                  45

Gly Met Ile Trp Gly Ala Asp Gly Asn Thr Asp Pro Asp Ser Val Lys
    50                  55                  60

Gly Arg Phe Thr Ile Ser Arg Glu Asn Thr Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Asp Phe Tyr Asp Tyr Asp Val Phe Tyr Tyr Ala Met Asp Tyr Trp
                100                 105                 110

Gly Gln Gly Thr Thr Val Thr Val Ser Ser
            115                 120

<210> SEQ ID NO 2
<211> LENGTH: 107
<212> TYPE: PRT
<213> ORGANISM: Artificial Sequence
<220> FEATURE:
<223> OTHER INFORMATION: Light chain variable region

<400> SEQUENCE: 2

Asp Ile Gln Leu Thr Gln Ser Pro Ser Thr Leu Ser Ala Ser Val Gly
1               5                   10                  15

Asp Arg Val Thr Ile Thr Cys Arg Ala Ser Gln Ser Val Gly Asn Asn
            20                  25                  30

Lys Leu Ala Trp Tyr Gln Gln Lys Pro Gly Lys Ala Pro Lys Leu Leu
        35                  40                  45

Ile Tyr Lys Ala Ser Asn Leu Ala Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Asp Asp Phe Ala Thr Tyr Tyr Cys Gln Gln His Asp Tyr Pro Tyr
                85                  90                  95

Thr Phe Gly Gln Gly Thr Lys Val Glu Ile Lys
                100                 105

<210> SEQ ID NO 3
<211> LENGTH: 118
<212> TYPE: PRT
<213> ORGANISM: Artificial Sequence
<220> FEATURE:
<223> OTHER INFORMATION: Heavy chain variable region

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Arg Ala Ser Gly Tyr Ala Ile Asn Gly Trp
            20                  25                  30

Val Arg Gln Ala Thr Gly Lys Gly Leu Glu Trp Val Ala Asn Ile Tyr
        35                  40                  45

Pro Gly Ser Gly Gly Thr Ala Pro Asp Ser Val Lys Gly Arg Phe Thr
    50                  55                  60

Ile Ser Arg Glu Asn Ala Lys Asn Ser Leu Val Leu Gln Met Asn Ser
65                  70                  75                  80

Leu Arg Ala Gly Asp Thr Ala Val Tyr Tyr Cys Ala Arg Asp Arg Tyr
```

```
                85                  90                  95
Ser Pro Thr Gly His Tyr Tyr Gly Met Asp Val Trp Gly Gln Gly Thr
            100                 105                 110

Thr Val Thr Val Ser Ser
        115

<210> SEQ ID NO 4
<211> LENGTH: 107
<212> TYPE: PRT
<213> ORGANISM: Artificial Sequence
<220> FEATURE:
<223> OTHER INFORMATION: Light chain variable region

<400> SEQUENCE: 4

Asp Ile Gln Met Thr Gln Ser Pro Ser Thr Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Asn Trp Tyr Gln Gln Lys Pro Gly Lys Ala Pro Lys Leu Leu Ile
        35                  40                  45

Tyr Gln Met Ser Asn Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Phe Asn Arg Tyr Pro Leu
                85                  90                  95

Thr Phe Gly Gln Gly Thr Lys Val Glu Ile Lys
            100                 105

<210> SEQ ID NO 5
<211> LENGTH: 13
<212> TYPE: PRT
<213> ORGANISM: Artificial Sequence
<220> FEATURE:
<223> OTHER INFORMATION: Heavy chain CDR of scFv3

<400> SEQUENCE: 5

Ser Val Thr Gly Glu Pro Ile Thr Ser Gly Phe Trp Asp
1               5                   10

<210> SEQ ID NO 6
<211> LENGTH: 9
<212> TYPE: PRT
<213> ORGANISM: Artificial Sequence
<220> FEATURE:
<223> OTHER INFORMATION: Heavy chain CDR of scFv3

<400> SEQUENCE: 6

Met Ile Trp Gly Ala Asp Gly Asn Tyr
1               5

<210> SEQ ID NO 7
<211> LENGTH: 14
<212> TYPE: PRT
<213> ORGANISM: Artificial Sequence
<220> FEATURE:
<223> OTHER INFORMATION: Heavy chain CDR of scFv3

<400> SEQUENCE: 7

Asp Phe Tyr Asp Tyr Asp Val Phe Tyr Tyr Ala Met Asp Tyr
1               5                   10
```

```
<210> SEQ ID NO 8
<211> LENGTH: 12
<212> TYPE: PRT
<213> ORGANISM: Artificial Sequence
<220> FEATURE:
<223> OTHER INFORMATION: Light chain CDR of scFv3

<400> SEQUENCE: 8

Arg Ala Ser Gln Ser Val Gly Asn Asn Lys Leu Ala
1               5                   10

<210> SEQ ID NO 9
<211> LENGTH: 8
<212> TYPE: PRT
<213> ORGANISM: Artificial Sequence
<220> FEATURE:
<223> OTHER INFORMATION: Light chain CDR of scFv3

<400> SEQUENCE: 9

Tyr Lys Ala Ser Asn Leu Ala Ser
1               5

<210> SEQ ID NO 10
<211> LENGTH: 8
<212> TYPE: PRT
<213> ORGANISM: Artificial Sequence
<220> FEATURE:
<223> OTHER INFORMATION: Light chain CDR of scFv3

<400> SEQUENCE: 10

Gln Gln His Asp Tyr Pro Tyr Thr
1               5

<210> SEQ ID NO 11
<211> LENGTH: 9
<212> TYPE: PRT
<213> ORGANISM: Artificial Sequence
<220> FEATURE:
<223> OTHER INFORMATION: Heavy chain CDR of scFv5

<400> SEQUENCE: 11

Arg Ala Ser Gly Tyr Ala Ile Asn Gly
1               5

<210> SEQ ID NO 12
<211> LENGTH: 10
<212> TYPE: PRT
<213> ORGANISM: Artificial Sequence
<220> FEATURE:
<223> OTHER INFORMATION: Heavy chain CDR of scFv5

<400> SEQUENCE: 12

Asn Ile Tyr Pro Gly Ser Gly Gly Thr Ala
1               5                   10

<210> SEQ ID NO 13
<211> LENGTH: 14
<212> TYPE: PRT
<213> ORGANISM: Artificial Sequence
<220> FEATURE:
<223> OTHER INFORMATION: Heavy chain CDR of scFv5

<400> SEQUENCE: 13

Asp Arg Tyr Ser Pro Thr Gly His Tyr Tyr Gly Met Asp Val
1               5                   10

<210> SEQ ID NO 14
```

```
<211> LENGTH: 11
<212> TYPE: PRT
<213> ORGANISM: Artificial Sequence
<220> FEATURE:
<223> OTHER INFORMATION: Light chain CDR of scFv5

<400> SEQUENCE: 14

Lys Ala Ser Gln Asp Ile Asn Ser Tyr Leu Asn
1               5                   10

<210> SEQ ID NO 15
<211> LENGTH: 8
<212> TYPE: PRT
<213> ORGANISM: Artificial Sequence
<220> FEATURE:
<223> OTHER INFORMATION: Light chain CDR of scFv5

<400> SEQUENCE: 15

Tyr Gln Met Ser Asn Leu Ala Ser
1               5

<210> SEQ ID NO 16
<211> LENGTH: 9
<212> TYPE: PRT
<213> ORGANISM: Artificial Sequence
<220> FEATURE:
<223> OTHER INFORMATION: Light chain CDR of scFv5

<400> SEQUENCE: 16

Gln Gln Phe Asn Arg Tyr Pro Leu Thr
1               5
```

ASTROTACTIN1-BASED COMPOSITIONS AND PHARMACEUTICAL FORMULATIONS

CROSS-REFERENCE TO RELATED APPLICATIONS

This application is a 35 U.S.C. § 371 national stage application of PCT International Application No. PCT/US2019/047596, filed Aug. 21, 2019, which claims the benefit of U.S. Provisional Application No. 62/720,138, filed Aug. 21, 2018, both of which are hereby incorporated by reference in their entirety.

FIELD

Provided herein are methods of detecting, preventing, treating, controlling or managing progressive neurodegenerative diseases in subjects in need thereof. The disclosed methods make use of antibodies that reduce or eliminate monocytes that abnormally express Astrotactin (ASTN1), or block blood monocytes that abnormally express ASTN1 from migrating to the central nervous system. Also provided are pharmaceutical compositions that comprise antibodies that specifically target the extracellular domain (ECD2) of ASTN1 for the prevention, treatment, control or management of progressive neurodegenerative diseases.

BACKGROUND

Neurodegenerative diseases are incurable and debilitating conditions characterized by a progressive loss of neurons in the central nervous system (CNS), which impairs brain functions, such as memory, movement and cognition, and eventually leads to severe debilitation and death. Neurodegenerative diseases, which include, among others, Alzheimer's disease (AD), Parkinson's disease (PD), amyotrophic lateral sclerosis (ALS), multiple sclerosis, Huntington's disease and multiple system atrophy, usually progress over a long period of time, and the actual onset of neurodegeneration may precede clinical manifestations by many years. Although the mechanism that regulates neurodegenerative diseases is not known, inflammation in the CNS seems to be a common feature in neurodegenerative diseases.

Astrotactins are membrane proteins named after their function in neuron-astroglial interactions during central nervous system (CNS) development. In mice and humans there are two astrotactin family members-astn-1 and astn-2 in mice, and ASTN1 and ASTN2 in humans. Astn1 knockout mice develop a small cerebellum and exhibit poor balance and coordination skills, apparently because of deficient migration of cerebellar granule cells and abnormal development of Purkinje cells. In humans, mutations affecting astrotactin genes have been reported in patients with different neurodevelopmental disorders, including developmental brain disorders, autism spectrum disorders, attention deficit hyperactivity disorder, obsessive-compulsive disorder, schizophrenia and cancer.

There is an urgent need for early detection, prophylactic treatment and effective cure of progressive neurodegenerative diseases. The present application presents a solution to the aforementioned challenges. In particular, the present inventors, with much efforts and experimentation, have successfully devised antibodies that neutralize blood monocytes expressing ASTN1 or block their migration into the CNS, and are effective in preventing or treating progressive neurodegenerative diseases.

SUMMARY

It is shown herein that subjects genetically prone to develop a progressive neurodegenerative disorder and subjects with a progressive neurodegenerative disorder abnormally express Astrotactin (ASTN1) in their blood monocytes. Based on these findings, antibodies to ASTN1 and antibody fragments that react with ASTN1 are provided. The disclosed antibodies and antibody fragments reduce or eliminate monocytes that abnormally express ASTN1, or block blood monocytes that abnormally express ASTN1 from migrating to the central nervous system.

In some embodiment, the disclosed antibodies or fragments thereof comprise a heavy chain VR and a light chain VR, wherein the heavy chain VR comprises an amino acid sequence of SEQ ID NO: 1, and wherein the light chain VR comprises an amino acid sequence of SEQ ID NO: 2.

In some embodiment, the disclosed antibodies or fragments thereof comprise a heavy chain VR and a light chain VR, wherein the heavy chain VR comprises an amino acid sequence of SEQ ID NO: 3, and wherein the light chain VR comprises an amino acid sequence of SEQ ID NO: 4.

The disclosed antibodies or fragments thereof may bind one or more residues in ASTN1 extracellular domain 1205-1208 region including, but not limited to, one or more residues are one or more of Gln1205, His1206, Tyr1207 and Glu1208.

In other embodiments, the disclosed antibodies or fragments thereof comprise a heavy chain VR and a light chain VR, wherein the heavy chain VR comprises heavy chain CDRs comprising anyone of SEQ ID NO: 5, SEQ ID NO: 6, or SEQ ID NO: 7, and wherein the light chain VR comprises light chain CDRs comprising anyone of SEQ ID NO: 8, SEQ ID NO: 9, or SEQ ID NO: 10.

In yet other embodiments, the disclosed antibodies or fragments thereof comprise a heavy chain VR and a light chain VR, wherein the heavy chain VR comprises heavy chain CDRs comprising anyone of SEQ ID NO: 11, SEQ ID NO: 12, or SEQ ID NO: 13, and wherein the light chain VR comprises light chain CDRs comprising anyone of SEQ ID NO: 14, SEQ ID NO: 15, or SEQ ID NO: 16.

The disclosed antibodies or fragments thereof may bind one or more residues in ASTN1 extracellular domain including, but not limited to, one or more of Phe757, Arg758, Gln759, Asn760, Asn761, Phe762, Ala763, Arg764, Gly765, Leu766, Asp767, Gln768, Gln769, Val775, Val776, Ala777, Thr778, Val808, Arg888, Arg911, Lys931, His932, Ala935, Thr1073, Asp1074, Arg1075, Met1076, Asp1077, His1078, Ser1079, Lys1080, Val1081, Glu1082, Thr1083, Thr1085, Leu1087, Asp1092, Ser1095, Gly1096, Ala1097, Lys1098, Ser1099, Pro1100, Cys1101, Ala1102, Ile1119, Glu1123, Pro1124, Lys1160, Glu1163, Ile1164, Lys1167, Asn1168, Thr1176, Gln1182, Thr1183, Tyr1185, Asn1186, Leu1189, Asp1190, Leu1191, Gly1192, Ser1193, Tyr1201, Gln1205, His1206, Glu1208, Ser1209, Glu1212, Trp1215, Glu1218, Pro1223, Arg1224, Gly1227, Leu1230, Ser1231, Gln1232, Gly1234, Asp1235, Gln1245, Glu1246, Pro1247, Tyr1296, Gly1297, Asp1298, Ser1299, or Lys1300.

Also provided herein are stable liquid aqueous pharmaceutical formulations that comprise the disclosed antibodies or fragments thereof, a tonicity agent, a surfactant, and a buffer.

In some embodiments, the liquid aqueous pharmaceutical formulations may optionally further comprise one or more pharmaceutically acceptable excipients, diluents, adjuvants, stabilizers, emulsifiers, preservatives, colorants, buffers, flavor-imparting agents or pharmaceutically acceptable carriers suitable for enteral, parenteral, or intravenous administration.

In additional embodiments, the liquid aqueous pharmaceutical formulations may further comprise one or more of a chemotherapeutic agent, an immunosuppressive agent, an immuno-stimulatory agent, an anti pyretic agent, a cytotoxic agent, a nucleolytic compound, a radioactive isotope, a receptor, a pro-drug activating enzyme, an anti-inflammatory agent, an antibiotic, a protease inhibitor, a growth factor, an osteo-inductive factor, an antibacterial agent or an antifungal agent.

In some embodiments, the liquid aqueous pharmaceutical formulations are in form of injectable depots.

In yet other embodiments, provided herein are methods of detecting, preventing, treating, controlling or managing a progressive neurodegenerative disease in a subject in need thereof, wherein the methods comprise the steps of (a) detecting expression of astrotactin (ASTN1) in the subject's blood monocytes; and (b) administering to the subject a therapeutically effective amount of the disclosed antibodies or fragments thereof.

The disclosed methods comprise administering to subjects in need thereof the disclosed antibodies or fragments thereof in form of a stable liquid aqueous pharmaceutical formulation comprising the antibody or fragment thereof, a tonicity agent, a surfactant, and a buffer.

In some embodiments, the liquid aqueous pharmaceutical formulations may optionally further comprise one or more pharmaceutically acceptable excipients, diluents, adjuvants, stabilizers, emulsifiers, preservatives, colorants, buffers, flavor-imparting agents or pharmaceutically acceptable carriers suitable for enteral, parenteral, or intravenous administration.

In some embodiments, the disclosed methods may further comprise administering to the subject one or more of a chemotherapeutic agent, an immunosuppressive agent, an immuno-stimulatory agent, an anti pyretic agent, a cytotoxic agent, a nucleolytic compound, a radioactive isotope, a receptor, a pro-drug activating enzyme, an anti-inflammatory agent, an antibiotic, a protease inhibitor, a growth factor, an osteo-inductive factor, an antibacterial agent or an antifungal agent.

In some embodiments, the progressive neurodegenerative disease is Alzheimer's Disease, Huntington's Disease, Amyotrophic Lateral Sclerosis, multiple sclerosis, multiple system atrophy, or Parkinson's Disease.

In some embodiments, the disclosed methods may further comprise detecting abnormally elevated expression of one or more cytokine, or one or more signaling pathway in the subject. In some examples, the cytokine is one or more of IL-1b, IL-6 or TNF. In some examples, the signaling pathway is one or more of Janus tyrosine Kinase (JAK) pathway, or Signal Transducer and Activator of Transcription (STAT) pathway.

In yet other embodiments, detecting expression of ASTN1 in the subject's blood monocytes may be performed by reconstructing an RNA transcriptome from a list of RNA reads of the subject and inputting the RNA transcriptome into a machine learning classifier trained to detect the expression of ASTN1.

In some examples, the disclosed methods comprise the use of a random forest classifier or other machine learning classifier to determine whether a subject is a candidate for treatment with the disclosed pharmaceutical formulations.

The foregoing and other features of the disclosure will become more apparent from the following detailed description of several embodiments, which proceeds with reference to the accompanying figure.

DETAILED DESCRIPTION

Figure 1:
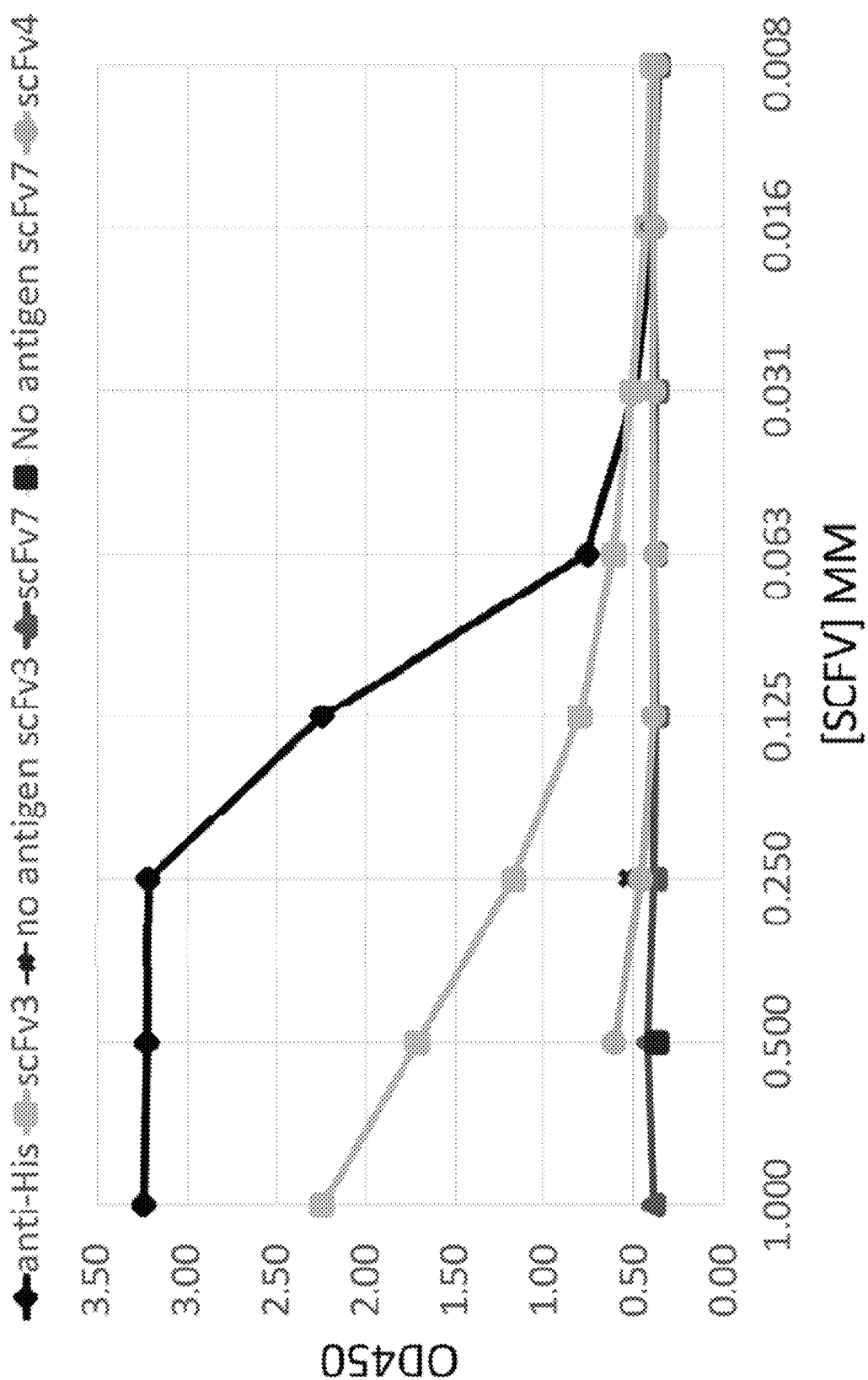
FIG. 1 is a graph representing the binding of the disclosed antibodies to the target ASTN1 antigen at different antibody concentration, as measured by optical density at 450 nm. Different variants of the disclosed antibodies and antibody fragments (ScFv) were designed, synthesized, cloned, codon-optimized for *Escherichia coli* expression, expressed in *E. coli*, extracted and only partially purified by NINTA (60-70% pure). Antigen (ASTN1)-ScFv interaction was determined by ELISA. ASTN1 was diluted to a final concentration of 40 ng/μl in PBS/1 mM $CaCl_2$, and 35 μL of the solution per well was coated on the wells of a PVC microtiter plate (96 wells). Uncoated wells served as negative control. The disclosed antibodies, antibody fragments and anti-His antibody were diluted to desired concentrations using blocking buffer as the diluent with a final volume of 50 μl and dispensed into the assigned wells. Each sample was run in several duplicates. ScFv3: full-length antibody in the presence of ASTN1; ScFv7: antibody fragment in the presence of ASTN1; anti-His: positive control (best binding in the presence of ASTN1); ScFv4: antibody fragment in the presence of ASTN1; no antigen-ScFv3: negative control (full-length antibody in the absence of ASTN1); no antigen-ScFv7: negative control (antibody fragment in the absence of ASTN1). The results show that, compared to the positive control, at a concentration of 250 nM there is detectable binding of the ScFv3 full-length antibody to ASTN1 even when the antibody is not fully purified, suggesting that the purified antibody will be even more effective at lower concentrations. Antibody fragments ScFv7 and ScFv4 were not effective. As expected, the negative controls showed no binding in the absence of ASTN1.

The following explanations of terms and methods are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. For example, reference to "comprising a therapeutic agent" includes one or a plurality of such therapeutic agents. The term "or" refers to a single element of stated alternative elements or a combination of two or more elements, unless the context clearly indicates otherwise. For example, the phrase "A or B" refers to A, B, or a combination of both A and B. Furthermore, the various elements, features and steps discussed herein, as well as other known equivalents for each such element, feature or step, can be mixed and matched by one of ordinary skill in this art to perform methods in accordance with principles described herein. Among the various elements, features, and steps some will be specifically included and others specifically excluded in particular examples.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. All references cited herein are incorporated by reference in their entirety.

In some examples, the numbers expressing quantities of ingredients, properties such as molecular weight, reaction conditions, and so forth, used to describe and claim certain embodiments are to be understood as being modified in some instances by the term "about" or "approximately." For example, "about" or "approximately" can indicate +/−20% variation of the value it describes. Accordingly, in some embodiments, the numerical parameters set forth herein are approximations that can vary depending upon the desired properties for a particular embodiment. Notwithstanding that the numerical ranges and parameters setting forth the broad scope of some examples are approximations, the numerical values set forth in the specific examples are reported as precisely as practicable. The recitation of ranges of values herein is merely intended to serve as a shorthand method of referring individually to each separate value falling within the range.

To facilitate review of the various embodiments of this disclosure, the following explanations of specific terms are provided:

Administer or Apply: To provide or give a subject a composition, such as a pharmaceutical composition, by an effective route. Exemplary routes of administration include, but are not limited to, parenteral, intravenous, and muscular routes.

Alzheimer's Disease (AD): An irreversible, progressive brain disorder that slowly destroys memory and thinking skills, and eventually the ability to carry out the simplest tasks. In most people with Alzheimer's, symptoms first appear in their mid-60s. AD is currently ranked as the sixth leading cause of death in the United States, and it is the most common cause of dementia among older adults. AD is associated with the formation of β amyloid plaques and neurofibrillary tangles of the tau protein in the brain and the loss of connections between neurons in the brain. The damage initially appears to take place in the hippocampus, and as more neurons die, additional parts of the brain are affected and begin to shrink. Memory problems are typically one of the first signs of cognitive impairment related to Alzheimer's disease. As AD progresses, memory loss confusion and inability to recognize familiar faces grow worse. Ultimately, plaques and tangles spread throughout the brain, and brain tissue shrinks significantly. Causes of AD probably include a combination of genetic, environmental, and lifestyle factors.

These plaques and tangles in the brain are still considered some of the main features of Alzheimer's disease. Another feature is the loss of connections between nerve cells (neurons) in the brain. Neurons transmit messages between different parts of the brain, and from the brain to muscles and organs in the body.

Amyotrophic Lateral Sclerosis (ALS): A progressive neurodegenerative disease that affects motor neurons in the brain and the spinal cord, with consequent muscle degeneration and atrophy. Sporadic ALS, the most common form of the disease in the U.S., accounts for 90 to 95 percent of all cases. Familial ALS (FALS) is genetically inherited and it accounts for 5 to 10 percent of all cases in the U.S. There is no cure for ALS.

Analog: A compound having a structure similar to another, but differing from it, for example, in one or more atoms, functional groups, or substructure.

Anesthetic agent: An active agent that causes reduction or loss of sensation.

Antagonist: A molecule that, upon binding to a cell receptor, competes and/or interferes with one or more ligands binding the same receptor, and thus reduces or prevents a response elicited by those ligands.

Antibiotic: A chemical substance capable of treating bacterial infections by inhibiting the growth of, or by destroying existing colonies of bacteria and other microorganisms.

Antibody: An immunoglobulin capable of specifically binding a target molecule, such as a carbohydrate, a polynucleotide, a lipid, or a polypeptide, via one or more antigen recognition sites, located in the variable region of the immunoglobulin molecule. The term "antibody" includes polyclonal and monoclonal antibodies, fragments thereof, such as Fab, Fab', F(ab')$_2$ and Fv, single chain variable fragments (ScFv), mutants thereof, fusion proteins comprising an antibody portion, and any other modified configuration of the immunoglobulin molecule that comprises an antigen recognition site. Antibodies can be distinguished into five major classes, IgA, IgD, IgE, IgG, and IgM, according to the amino acid sequence of the constant domain in their heavy chains. Monoclonal antibodies are obtained from a substantially homogeneous population of antibodies, and specifically target a single epitope (determinant) of an antigen. Polyclonal antibodies target different epitopes on the antigen. The heavy and light chains of an antibody each comprise a variable region and a constant region. The variable regions of the heavy and light chain each consist of four framework regions (FR) connected by three complementarity-determining regions (CDRs), also known as hypervariable regions. The CDRs in each chain are held together in close proximity by the FRs and form the antibody's antigen-binding site. The constant regions of the heavy and light chains of an antibody provide structural stability and are not involved in antigen binding.

Antibody-Dependent Cell-Mediated Cytotoxicity (ADCC): A cell-mediated reaction in which nonspecific cytotoxic cells that express Fc receptors (FcRs), such as natural killer (NK) cells, neutrophils, and macrophages, recognize bound antibody on a target cell and subsequently cause lysis of the target cell.

Antibody-drug conjugate (ADC): Complex molecules composed of an antibody linked to a biologically active cytotoxic payload or drug. By combining the targeting capabilities of monoclonal antibodies with the cancer-killing ability of cytotoxic drugs, antibody-drug conjugates allow for discrimination between healthy and diseased tissue. Unlike traditional chemotherapeutic drugs, antibody-drug conjugates target only cancer cells so that healthy cells are less severely affected.

Anti-Fungal Agent: An active agent capable of inhibiting the growth of or destroying fungi.

Anti-inflammatory agent: An active agent that reduces inflammation and swelling.

Anti-Oxidant: An active agent that inhibits oxidation or reactions promoted by oxygen or peroxides.

Anti-Protozoal Agent: An active agent capable of inhibiting the growth of or destroying protozoa microorganisms.

Antipruritic Agent: An active agent that reduces, eliminates or prevents itching.

Anti-Viral Agent: An active agent that inhibits the replication of or destroys viruses.

Astrotactin (Astn1): ASTN1 is a transmembrane protein and a member of the Perforin-like Protein (PLP) family, which is involved in regulation of adhesion in the radial migration of neurons during the development of CNS. ASTN1 is expressed on neuronal granule cells, which are precursor neurons that move through the brain to sites of injury, tissue repair or growth. Neuronal granule cells express ASTN1 to access a 'glial monorail system' in the brain, in which they move from glial cell to glial cell by following chemotactic or growth factor gradients.

Binding Site or Binding Domain: A region on a protein, DNA or RNA, to which specific molecules and/or ions (ligands) may form a chemical bond. Characteristics of binding sites are chemical specificity, a measure of the types of ligands that will bond, and affinity, which is a measure of the strength of the chemical bond.

Blood-Brain Barrier: A highly selective semipermeable border that separates circulating blood from the brain and extracellular fluid in the central nervous system (CNS). The blood-brain barrier, formed by endothelial cells, allows the passage of water, some gases, and lipid-soluble molecules by passive diffusion, and the selective transport of molecules such as glucose and amino acids that are crucial to neural function. The blood-brain barrier restricts the diffusion of solutes in the blood and large or hydrophilic molecules into the cerebrospinal fluid (CSF), while allowing the diffusion of hydrophobic molecules and small polar molecules.

Cancer: A condition characterized by unregulated cell growth. Examples of cancer include, but are not limited to, squamous cell cancer, small-cell lung cancer, non-small cell lung cancer, lung adenocarcinoma, lung squamous cell carcinoma, gastrointestinal cancer, Hodgkin's and non-Hodgkin's lymphoma, pancreatic cancer, glioblastoma, cervical cancer, glioma, ovarian cancer, liver cancer such as hepatic carcinoma and hepatoma, bladder cancer, breast cancer, colon cancer, colorectal cancer, endometrial or uterine carcinoma, salivary gland carcinoma, kidney cancer such as renal cell carcinoma and Wilms' tumors, basal cell carcinoma, melanoma, prostate cancer, thyroid cancer, testicular cancer, esophageal cancer, and various types of head and neck cancer.

Chemotherapeutic agent or Chemotherapy: A chemical agent with therapeutic usefulness in the treatment of diseases characterized by abnormal cell growth. Such diseases include tumors, neoplasms, and cancer. In one example, a chemotherapeutic agent is a radioactive compound. Chemotherapeutic agents include, but are not limited to, biologics, such as monoclonal antibodies. In some examples, a subject treated with an active agent using the disclosed methods, is, will be, or was previously treated with chemotherapy.

Chimeric Antibody: An antibody having a variable region or part of variable region from a first species of a mammal and a constant region from a second species of a mammal.

Complementarity-Determining Regions (CDRs): CDRs are part of the variable chains in antibodies and T cell receptors, that are generated by B cells and T cells, respectively, where these molecules bind to their specific antigen. A set of CDRs constitutes a paratope. CDRs determine antigen specificities.

Contacting: Placement in direct physical association; includes both in solid and liquid form. Contacting can occur in vitro with isolated cells (for example in a tissue culture dish or other vessel) or in vivo by administering an active agent to a subject.

Control: A reference standard. In some examples, a control is a known value or range of values, such as one indicative of the presence or the absence of Huntington's disease. In some examples, a control is a value or range of values, indicating a response in the absence of a therapeutic agent.

Cross-linked: A composition containing intramolecular and/or intermolecular crosslinks, whether arising through covalent or non-covalent bonding. "Non-covalent" bonding includes both hydrogen bonding and electrostatic (ionic) bonding.

Cytokine: A substance released by one cell population that acts on another cell as intercellular mediator. Examples of cytokines include, but are not limited to, lymphokines, monokines; interleukins (Ms) such as IL-1, IL-1α, IL-2, IL-3, IL-5, IL-6, IL-7, IL-8, IL-9, IL-11, IL-12, IL-15, including PROLEUKIN® rIL-2; a tumor necrosis factor such as TNF-α or TNF-β; and other polypeptide factors including LIF and kit ligand (KL).

Cytotoxic agent: A substance that inhibits or prevents the function of cells and/or causes destruction of cells.

Domain: A distinct functional and/or structural unit of a protein. A conserved domain refers to a domain that has been conserved during evolution. During evolution, changes at specific positions of an amino acid sequence in the protein have occurred in a way that preserve the physico-chemical properties of the original residues, and hence the structural and/or functional properties of that region of the protein.

Drug or Active Agent: A chemical substance or compound that induces a desired pharmacological or physiological effect, and includes therapeutically effective, prophylactically effective, or systematically effective agents. The terms also encompass pharmaceutically acceptable, pharmacologically active derivatives and analogs of those active agents specifically mentioned herein, including, but not limited to, salts, esters, amides, pro-drugs, active metabolites, inclusion complexes, analogs, and the like. Suitable active agents that may be incorporated into the pharmaceutical compositions provided herein include, but are not limited to, adrenergic agents; adrenocortical steroids; adrenocortical suppressants; alcohol deterrents; aldosterone antagonists; amino acids; ammonia detoxicants; anabolic agents; analeptic agents; analgesic agents; androgenic agents; anesthetic agents; anorectic compounds; anorexic agents; antagonists; anterior pituitary activators and anterior pituitary suppressants; anti-acne agents; anti-adrenergic agents; anti-allergic agents; anti-amebic agents; anti-androgen agents; anti-anemic agents; anti-anginal agents; anti-anxiety agents; anti-arthritic agents; anti-asthmatic agents and other respiratory drugs; anti-atherosclerotic agents; anti-bacterial agents; anticancer agents, including antineoplastic drugs, and anticancer supplementary potentiating agents; anticholinergics; anticholelithogenic agents; anti-coagulants; anti-coccidal agents; anti-convulsants; anti-depressants; anti-diabetic agents; anti-diarrheals; anti-diuretics; antidotes; anti-dyskinetics agents; anti-emetic agents; anti-epileptic agents; anti-estrogen agents; anti-fibrinolytic agents; anti-fungal agents; anti-glaucoma agents; antihelminthics; anti-hemophilic agents; anti-hemophilic Factor; anti-hemorrhagic agents; antihistamines; anti-hyperlipidemic agents; anti-hyperlipoproteinemic agents; antihypertensive agents; anti-hypotensives; anti-infective agents such as antibiotics and antiviral agents; anti-inflammatory agents, both steroidal and nonsteroidal; anti-keratinizing agents; anti-malarial agents; antimicrobial agents; anti-migraine agents; anti-mitotic agents; anti-mycotic agents; antinauseants; antineoplastic agents; anti-neutropenic agents; anti-obsessional agents; anti-parasitic agents; antiparkinsonism drugs; anti-pneumocystic agents; anti-proliferative agents; anti-prostatic hypertrophy drugs; anti-protozoal agents; antipruritics; anti-psoriatic agents; antipsychotics; antipyretics; antispasmodics; anti-rheumatic agents; anti-schistosomal agents; anti-seborrheic agents; anti-spasmodic agents; anti-tartar and anti-calculus agents; anti-thrombotic agents; anti-tubercular agents; anti-tussive agents; anti-ulcerative agents; anti-urolithic agents; antiviral agents; GERD medications, anxiolytics; appetite suppressants; attention deficit disorder (ADD) and attention deficit hyperactivity disorder (ADHD) drugs; bacteriostatic and bactericidal agents; benign prostatic hyperplasia therapy agents; blood glucose regulators; bone resorption inhibitors; bronchodilators; carbonic anhydrase inhibitors; cardiovascular preparations including anti-anginal agents, anti-arrhythmic agents, beta-blockers, calcium channel blockers, cardiac depressants, cardiovascular agents, cardioprotectants, and cardiotonic agents; central nervous system (CNS) agents; central nervous system stimulants; choleretic agents; cholinergic agents; cholinergic agonists; cholinesterase deactivators; coccidiostat agents; cognition adjuvants and cognition enhancers; cough and cold preparations, including decongestants; depressants; diagnostic aids; diuretics; dopaminergic agents; ectoparasiticides; emetic agents; enzymes which inhibit the formation of plaque, calculus or dental caries; enzyme inhibitors; estrogens; fibrinolytic agents; fluoride anticavity/antidecay agents; free oxygen radical scavengers; gastrointestinal motility agents; genetic materials; glucocorticoids; gonad-stimulating principles; hair growth stimulants; hemostatic agents; herbal remedies; histamine H2 receptor antagonists; hormones; hormonolytics; hypnotics; hypocholesterolemic agents; hypoglycemic agents; hypolipidemic agents; hypotensive agents; HMGCoA reductase inhibitors; immunizing agents; immunomodulators; immunoregulators; immunostimulants; immunosuppressants; impotence therapy adjuncts; inhibitors; keratolytic agents; leukotriene inhibitors; LHRH agonists; liver disorder treatments; luteolysin agents; memory adjuvants; mental performance enhancers; metal chelators such as ethylenediaminetetraacetic acid, tetrasodium salt; mitotic inhibitors; mood regulators; mucolytics; mucosal protective agents; muscle relaxants; mydriatic agents; narcotic antagonists; nasal decongestants; neuroleptic agents; neuromuscular blocking agents; neuroprotective agents; nicotine; NMDA antagonists; non-hormonal sterol derivatives; nutritional agents, such as vitamins, essential amino acids and fatty acids; ophthalmic drugs such as antiglaucoma agents; oxytocic agents; pain relieving agents; parasympatholytics; peptide drugs; plasminogen activators; platelet activating factor antagonists; platelet aggregation inhibitors; post-stroke and post-head trauma treatments; potentiators; progestins; prostaglandins; prostate growth inhibitors; proteolytic enzymes as wound cleansing agents; prothyrotropin agents; psychostimulants; psychotropic agents; radioactive agents; regulators; relaxants; repartitioning agents; scabicides; sclerosing agents; sedatives; sedative-hypnotic agents; selective adenosine A1 antagonists; serotonin antagonists; serotonin inhibitors; serotonin receptor antagonists; steroids, including progestogens, estrogens, corticosteroids, androgens and anabolic agents; smoking cessation agents; stimulants; suppressants; sympathomimetics; synergists; thyroid hormones; thyroid inhibitors; thyromimetic agents; tranquilizers; tooth desensitizing agents; tooth whitening agents such as peroxides, metal chlorites, perborates, percarbonates, peroxyacids, and combinations thereof; unstable angina agents; uricosuric agents; vasoconstrictors; vasodilators including general coronary, peripheral and cerebral; vulnerary agents; wound healing agents; xanthine oxidase inhibitors; and the like.

Effective amount: The amount of an active agent (alone or with one or more other active agents) sufficient to induce a desired response, such as to prevent, treat, reduce and/or ameliorate a progressive neurodegenerative disorder. Effective amounts of an active agent, alone or with one or more other active agents, can be determined in many different ways, such as assaying for a reduction in of one or more signs or symptoms associated with the condition, such as an uncontrolled inflammatory response condition, in the subject or measuring the level of one or more molecules associated with the condition to be treated.

Emulsifying Agents: Surfactants that reduce the interfacial tension between oil and water, minimizing the surface energy through formation of globules. Examples include, but are not limited to, glyceryl monostearate, methylcellulose, sodium lauryl sulfate, sodium oleate, sorbitan monopalmitate, sorbitan monostearate, sorbitan tristrearate, tragacanth, triethanolamine oleate, polyethylene sorbitan monolaurate, poloxamer, and any combination thereof.

Granule Cells: Cells within the granular layer of the cerebellum, the dentate gyms of the hippocampus, the superficial layer of the dorsal cochlear nucleus, the olfactory bulb, and the cerebral cortex. Cerebellar granule cells account for the majority of neurons in the human brain.

Humanized Antibody: A human immunoglobulin comprising some residues from a CDR of a non-human species, such as a mouse, rat, or rabbit, that has the desired specificity, affinity, and capacity, in place of some of the residues from a human complementary determining region (CDR). A humanized antibody may also comprise residues that are included to optimize antibody performance.

Huntington's Disease (HD): A fatal genetic disorder that causes the progressive breakdown of nerve cells in the brain and the deterioration of a person's physical and mental abilities. Every child of a parent with HD has a 50/50 chance of carrying the faulty gene. HD has no cure. Today, there are approximately 30,000 symptomatic Americans and more than 200,000 at-risk of inheriting the disease. Symptoms usually appear between the ages of 30 to 50, and worsen over a 10 to 25 year period. They include personality changes, mood swings, depression, forgetfulness, impaired judgment, unsteady gait, involuntary movements, slurred speech, difficulty in swallowing and significant weight loss.

Hydrogel: A water-swellable polymeric matrix that can absorb a substantial amount of water to form elastic gels. The matrix is a three-dimensional network of macromolecules held together by covalent or non-covalent crosslinks. Upon placement in an aqueous environment, dry hydrogels swell to the extent allowed by the degree of cross-linking.

Hydrogel Composition: A composition that either contains a hydrogel or is entirely composed of a hydrogel. Thus, "hydrogel compositions" encompass not only hydrogels per se but also compositions that comprise a hydrogel and one or more non-hydrogel components or compositions, e.g., hydrocolloids, which contain a hydrophilic component (which may contain or be a hydrogel) distributed in a hydrophobic phase.

Hydrophilic: A polymer, substance or compound that is capable of absorbing more than 10%/w of water at 100% relative humidity (rh).

Hydrophobic: A polymer, substance or compound that is capable of absorbing no more than 1%/w of water at 100% relative humidity (rh).

Hygroscopic: A polymer, substance or compound that is capable of absorbing more than 20 wt % of water at 100% relative humidity (rh).

Inhibiting a condition: Reducing, slowing, or even stopping the development of a condition, for example, in a subject who is at risk of developing or has a particular condition, such as a progressive neurodegenerative disease.

Interferon-gamma: IFN-$\gamma$, or type II interferon, is a cytokine inducing macrophages and Class II major histocompatibility complex (MEW) molecule expression. Aberrant IFN$\gamma$ expression is associated with a number of autoinflammatory and autoimmune diseases. IFN$\gamma$ is produced predominantly by natural killer (NK) and natural killer T (NKT) cells as part of the innate immune response, and by CD4 Th1 and CD8 cytotoxic T lymphocyte (CTL) effector T cells once antigen-specific immunity develops.

Interferon-type I: a large group of interferon proteins that bind to interferon receptors and regulate the activity of the immune system.

Keratolytic Agent: An agent that that thins or softens the skin. Exemplary keratolytic agents include urea, lactic acid, allantoin, benzoyl peroxide, salicyclic acid, sulfur, tretinoin, fluorouracil, trichloroacetic acid, and glycolic acid.

Lipophilic: A substance or compound that has an affinity for a non-polar environment compared to a polar or aqueous environment.

Localized application: The application of an active agent in a particular location in the body.

Monocytes: The largest type of leukocytes or white blood cells, which can differentiate into macrophages and myeloid lineage dendritic cells. Monocytes are produced by the bone marrow from monoblasts, which differentiate from hematopoietic stem cells. Monocytes circulate in the bloodstream for about one to three days and then typically move into tissues throughout the body where they differentiate into macrophages and dendritic cells. Monocytes and their macrophage and dendritic-cell progeny serve three main functions in the immune system: phagocytosis, antigen presentation, and cytokine production. Phagocytosis is the process of uptake of microbes and particles followed by digestion and destruction of this material. Monocytes are also capable of killing infected host cells via antibody-dependent cell-mediated cytotoxicity.

Mucosa: A membrane that lines various cavities in the body and covers the surface of internal organs. It consists of one or more layers of epithelial cells overlying a layer of loose connective tissue. The mucosa is mostly of endodermal origin and is continuous with the skin at various body openings such as the eyes, ears, inside the nose, inside the mouth, lip, vagina, the urethral opening and the anus. Some mucous membranes secrete mucus, a thick protective fluid. The function of the membrane is to stop pathogens and dirt from entering the body and to prevent bodily tissues from becoming dehydrated.

Multiple sclerosis (MS): A progressive neurodegenerative disorder that involves an immune-mediated process in which the body's immune system is directed against myelin, a protective coating of nerve fibers in the CNS, the nerve fibers and the cells that produce myelin. The damage may produce a variety of neurological symptoms. The cause of MS is not known, and there is no cure for MS.

Multiple system atrophy (MSA): A rare, degenerative neurologic condition that affects both men and women, usually starting in the 50's or early 60's. Similar to Parkinson's disease, MSA affects cells that produce dopamine, a neurotransmitter that controls motor commands. In addition, MSA affects both neurons and glial cells.

Neuron: An electrically excitable cell that receives, processes, and transmits information through electrical and chemical signals via specialized connections called synapses. Neurons are the primary components of the central nervous system, which includes the brain and spinal cord, and of the peripheral nervous system, which comprises the autonomic nervous system and the somatic nervous system. Sensory neurons respond to touch, sound, or light and convert the stimulus into an electrical signal via transduction, which is then sent to the spinal cord or brain. Motor neurons receive signals from the brain and spinal cord to control muscle contractions and glandular output. Interneurons connect neurons to other neurons within the same region of the brain or spinal cord in neural networks. A typical neuron consists of a cell body (soma), dendrites, and an axon. Dendrites are thin structures that arise from the cell body, often extending for hundreds of micrometers and branching multiple times, giving rise to a complex "dendritic tree". Axons are special cellular extensions that travel for a distance. Numerous axons are often bundled into fascicles that make up the nerves in the peripheral nervous system. Neurons are generated by stem cells during brain development and childhood. Neurons in the adult brain generally do not undergo cell division. Astrocytes are star-shaped glial cells, which are non-neuronal cells that maintain homeostasis, form myelin, and provide support and protection for neurons in the central and peripheral nervous systems.

Oil: Any fatty substance that is in liquid form at room temperature (25° C.) and at atmospheric pressure (760 mmHg). An oily phase in a pharmaceutical composition may comprise at least one polar or apolar hydrocarbon-based oil.

Parenteral: a type of administration that includes subcutaneous injections, intravenous, intramuscular, intrasternal injection or infusion techniques. Compositions for parenteral injection comprise pharmaceutically acceptable sterile aqueous or nonaqueous solutions, dispersions, suspensions or emulsions as well as sterile powders for reconstitution into sterile injectable solutions or dispersions prior to use.

Parkinson's Disease (PD): A brain disorder that leads to shaking, stiffness, difficulty with walking, balance, and coordination, mental and behavioral changes, sleep problems, depression, memory difficulties, and fatigue. Parkinson's symptoms usually begin gradually and get worse over time. The disease affects about 50 percent more men than women, and its typical onset occurs at about age 60. PD is triggered when neurons in the brain die, with consequent reduction in the production of dopamine and norepinephrine. The lack of dopamine causes the movement problems associated with PD, and the loss of norepinephrine leads to fatigue, irregular blood pressure, decreased movement of food through the digestive tract, and sudden drop in blood pressure when a person stands up from a sitting or lying-down position. Symptoms of PD include, but are not limited to, tremor in hands, arms, legs, jaw, or head; stiffness of the limbs and trunk; slowness of movement; impaired balance and coordination; depression; difficulty swallowing, chewing, and speaking; urinary problems or constipation, skin problems; and sleep disruptions. The main therapy for Parkinson's is levodopa to produce dopamine, in combination with carbidopa to prevent or reduce some of the side effects of levodopa. Once this therapy is no longer effective, subjects with PD are treated with dopamine agonists, MAO-B inhibitors, COMT inhibitors, Amantadine, and/or anticholinergic drugs to slow progression of the disease. There are currently no blood or laboratory tests to diagnose non-genetic cases of Parkinson's disease and there is no cure for Parkinson's disease.

Permeation Enhancer: A natural or synthetic molecule that facilitates the transport of co-administered active agents across biological membranes.

pH Modifier: A molecule or buffer used to achieve desired pH control in a formulation. Exemplary pH modifiers include acids (e.g., acetic acid, adipic acid, carbonic acid, citric acid, fumaric acid, phosphoric acid, sorbic acid, succinic acid, tartaric acid, basic pH modifiers (e.g., magnesium oxide, tribasic potassium phosphate), and pharmaceutically acceptable salts thereof.

Pharmaceutically acceptable carriers: The pharmaceutically acceptable carriers useful in this disclosure are conventional. *Remington's Pharmaceutical Sciences*, by E. W. Martin, Mack Publishing Co., Easton, Pa., 19th Edition (1995), describes compositions and formulations suitable for pharmaceutical delivery of the compositions herein disclosed. The nature of the carrier can depend on the particular mode of administration being employed. For instance, parenteral applications usually include pharmaceutically and physiologically acceptable fluids such as water, physiological saline, balanced salt solutions, aqueous dextrose, glycerol or the like as a vehicle. In addition to biologically-neutral carriers, parenteral compositions may also contain minor amounts of non-toxic auxiliary substances, such as wetting or emulsifying agents, preservatives, and pH buffering agents and the like.

Plasticizer: A material that, when added to a polymer, imparts an increase in flexibility, workability, and other properties to the finished product. Exemplary plasticizers include, but are not limited to, glycerol, sorbitol, polyethylene glycol, polypropylene glycol, polyethylene-propylene glycol, and any combination thereof.

Polymer: Includes homopolymers, linear and branched polymer structures, crosslinked polymers, copolymers (which may or may not be crosslinked), block copolymers, alternating copolymers, random copolymers, and the like. Oligomers are polymers having a molecular weight below about 1000 Da.

Proinflammatory cytokines: cytokines produced predominantly by activated macrophages and involved in the up-regulation of inflammatory reactions. Exemplary proinflammatory cytokines include, but are not limited to, IL-1β, IL-6, and TNF-α. IL-1β is released primarily by monocytes and macrophages during cell injury, infection, invasion, and inflammation. IL-1β expression is enhanced following crush injury to peripheral nerve and after trauma in microglia and astrocytes in the central nervous system (CNS), and can produce hyperalgesia following either intraperitoneal, intracerebroventricular or intraplantar injection. IL-6 plays a role in the neuronal reaction to nerve injury. There is evidence that IL-6 contributes to the development of neuropathic pain behavior following a peripheral nerve injury. TNF-α, also known as cachectin, is an inflammatory cytokine that acts on several different signaling pathways through two cell surface receptors, TNFR1 and TNFR2, to regulate apoptotic pathways, NF-kB activation of inflammation, and activate stress-activated protein kinases (SAPKs).

Skin: The largest organ in the body consisting of several layers. The skin plays an important role in biologic homeostasis, and is comprised of the epidermis and the dermis. The epidermis, which is composed of several layers beginning with the stratum corneum, is the outermost layer of the skin, and the deep dermis is the innermost skin layer. The skin has multiple functions, including thermal regulation, metabolic function (vitamin D metabolism), and immune functions. In humans, the usual thickness of the skin is 1-2 mm, although in some areas the skin may be more than 5 mm thick.

The epidermis provides the body's buffer zone against the environment and protection from trauma, excludes toxins and microbial organisms, and constitutes a semi-permeable membrane. The stratum corneum is an avascular, multilayer structure that functions as a barrier to the environment and prevents trans-epidermal water loss. Below the stratum corneum are the stratum lucidum, stratum granulosum, stratum germinativum, and stratum basale, each containing living cells with specialized functions. Dermal appendages, which include hair follicles, sebaceous and sweat glands, fingernails, and toenails, originate in the epidermis and protrude into the dermis hair follicles. The sebaceous glands are responsible for secretions that lubricate the skin, and sweat gland secretions control skin pH to prevent dermal infections. The sweat glands, dermal blood vessels, and small muscles control temperature on the surface of the body. Nerve endings in the skin include receptors for pain, touch, heat, and cold. The basement membrane separates and connects the epidermis and dermis. The dermis is a vascular structure that supports and nourishes the epidermis. In addition, there are sensory nerve endings in the dermis that transmit signals regarding pain, pressure, heat, and cold. The superficial dermis consists of extracellular matrix (collagen, elastin, and ground substances) and contains blood vessels, lymphatics, epithelial cells, connective tissue, muscle, fat, and nerve tissue. The vascular supply of the dermis is responsible for nourishing the epidermis and regulating body temperature. Fibroblasts are responsible for producing the collagen and elastin components of the skin, which give the skin its turgor. Fibronectin and hyaluronic acid are secreted by the fibroblasts. The deep dermis is located over the subcutaneous fat; it contains larger networks of blood vessels and collagen fibers to provide tensile strength. It also consists of fibroelastic connective tissue, which is composed mainly of collagen.

Skin Simulating Membrane: A semi-permeable membrane used to replicate the skin in diffusion testing.

Subject: A living multi-cellular vertebrate organism, a category that includes human and non-human mammals, as well as birds (such as chickens and turkeys), fish, and reptiles. Exemplary subjects include mammals, such as human and non-human primates, rats, mice, dogs, cats, rabbits, cows, pigs, goats, horses, and the like.

Surface or Body Surface: A surface located on the human body or within a body orifice. Thus, a "body surface" includes, by way of example, skin, teeth, skin or mucosal tissue, including the interior surface of body cavities that have a mucosal lining.

Transcriptome: A collection of all RNA transcripts obtained from one cell or a multiplicity of cells. The RNAs may comprise a mixture of different sequences.

Under conditions sufficient to: A phrase that is used to describe any environment that permits the desired activity.

Water-Insoluble: A polymer, compound or composition with a solubility in water of less than 5%/w, less than 3%/w, or less than 1%/w, as measured in water at 20° C.

Water-Swellable: A polymer, substance or compound, that may absorb an amount of water greater than at least 25%/w of its own weight, or greater than at least 50%/w, upon immersion in an aqueous medium.

Monoclonal Antibodies and Fragments Thereof that Bind ASTN1

The blood-brain barrier (BBB) is a membrane that restricts passage of cells, monocytes and macrophages from the blood to the brain. The membrane protects the brain from inflammation and proinflammatory molecules, such as cytokines. However, when the blood-brain barrier does not function properly, monocytes and macrophages gain access to the CNS, triggering the activation of microglia, the innate immune cells in the CNS, which in turn produce and secrete proinflammatory cytokines, reactive free radicals and proteases that alter neuron function.

Astrotactin (ASTN1) is a transmembrane protein and a member of the perforin like protein (PLP) family. PLPs play a role in pathogenic attack and immunological defense. ASTN1 is mainly expressed in neuronal granule cells in the cerebellum and the cerebral cortex, and it is localized in both the cell membrane and endosomal compartments. Neuronal granule cells are precursor neurons that move through the brain to sites of injury, tissue repair or growth. ASTN1 expression allows neuronal granule cells to move from glial cell to glial cell within the brain, a movement that is regulated by chemotactic and growth factor gradients. ASTN1 is a membrane-spanning protein, characterized by the presence of two transmembrane helices, a cytosolic domain and an extracellular region (EC2), which contains a small N-terminal domain and a large C-terminal domain. The ECD2 region, which faces outward from the cell to the blood fluid, allows cells expressing ASTN1 to interact with other cells and proteins. ASTN1 is normally expressed only in neuronal cells in the brain.

The present inventors have identified the presence of ASTN1 in blood monocytes as a major factor in the development of progressive neurological diseases. Monocytes are precursors to macrophages, and are part of the same myeloid cell lineage from which glial and astrocyte cells in the brain originate. Specifically, the present inventors have surprisingly and unexpectedly discovered that in individuals with a progressive neurodegenerative diseases and in individuals genetically prone to develop a progressive neurodegenerative disease blood monocytes express ASTN1, respond to chemical signals and are able to penetrate the brain through the blood brain barrier. Once in the brain, monocytes expressing ASTN1 may move through the brain to sites of injury, producing proinflammatory cytokines, and thus triggering or amplifying progressive neurodegenerative disease.

Based on these findings, the present inventors designed and developed monoclonal antibodies against epitopes on the extracellular domain 2 (ECD2) of the ASTN1 protein. The disclosed antibodies are capable of neutralizing, reducing or eliminating monocytes that abnormally express ASTN1, or block blood monocytes that abnormally express ASTN1 from migrating to the central nervous system.

The disclosed antibodies and fragments thereof comprise a heavy chain VR and a light chain VR.

In some embodiment, the heavy chain VR comprises an amino acid sequence of SEQ ID NO: 1, and the light chain VR comprises an amino acid sequence of SEQ ID NO: 2.

In some embodiment, the heavy chain VR comprises an amino acid sequence of SEQ ID NO: 3, and the light chain VR comprises an amino acid sequence of SEQ ID NO: 4.

The disclosed antibodies or fragments thereof may bind one or more residues in ASTN1 extracellular domain 1205-1208 region including, but not limited to, one or more residues are one or more of Gln1205, His1206, Tyr1207 and Glu1208.

In other embodiments, the disclosed antibodies or fragments thereof comprise a heavy chain VR and a light chain VR, wherein the heavy chain VR comprises heavy chain CDRs comprising anyone of SEQ ID NO: 5, SEQ ID NO: 6, or SEQ ID NO: 7, and wherein the light chain VR comprises light chain CDRs comprising anyone of SEQ ID NO: 8, SEQ ID NO: 9, or SEQ ID NO: 10.

In yet other embodiments, the disclosed antibodies or fragments thereof comprise a heavy chain VR and a light chain VR, wherein the heavy chain VR comprises heavy chain CDRs comprising anyone of SEQ ID NO: 11, SEQ ID NO: 12, or SEQ ID NO: 13, and wherein the light chain VR comprises light chain CDRs comprising anyone of SEQ ID NO: 14, SEQ ID NO: 15, or SEQ ID NO: 16.

The disclosed antibodies or fragments thereof may bind one or more residues in ASTN1 extracellular domain including, but not limited to, one or more of Phe757, Arg758, Gln759, Asn760, Asn761, Phe762, Ala763, Arg764, Gly765, Leu766, Asp767, Gln768, Gln769, Val775, Val776, Ala777, Thr778, Val808, Arg888, Arg911, Lys931, His932, Ala935, Thr1073, Asp1074, Arg1075, Met1076, Asp1077, His1078, Ser1079, Lys1080, Val1081, Glu1082, Thr1083, Thr1085, Leu1087, Asp1092, Ser1095, Gly1096, Ala1097, Lys1098, Ser1099, Pro1100, Cys1101, Ala1102, Ile1119, Glu1123, Pro1124, Lys1160, Glu1163, Ile1164, Lys1167, Asn1168, Thr1176, Gln1182, Thr1183, Tyr1185, Asn1186, Leu1189, Asp1190, Leu1191, Gly1192, Ser1193, Tyr1201, Gln1205, His1206, Glu1208, Ser1209, Glu1212, Trp1215, Glu1218, Pro1223, Arg1224, Gly1227, Leu1230, Ser1231, Gln1232, Gly1234, Asp1235, Gln1245, Glu1246, Pro1247, Tyr1296, Gly1297, Asp1298, Ser1299, or Lys1300.

The disclosed antibodies and fragments thereof may be conjugated with a cytotoxic drug to form antibody-drug conjugates (ADCs), such that the disclosed antibodies or fragments thereof may detect ASTN1 and attach to the surface of blood monocytes carrying ASTN1. The biochemical reaction between the antibody and ASTN1 triggers a signal in the blood monocytes, which then absorb or internalize the antibody together with the cytotoxic drug. Once the ADC is internalized, the cytotoxic drug is released and kills the blood monocytes carrying ASTN1.

Pharmaceutical Compositions Comprising Monoclonal Antibodies and Fragments Thereof that Bind ASTN1

Also provided herein are stable liquid aqueous pharmaceutical formulations that comprise the disclosed antibodies or fragments thereof, in combination with a tonicity agent, a surfactant, and a buffer, for the prevention, treatment, control or management of progressive neurological diseases in subjects in need thereof.

The disclosed pharmaceutical compositions may be formulated for parenteral or intravenous administration. Parenteral administration may include subcutaneous injections, intravenous, intramuscular, intrasternal injection or infusion techniques. Micelles or liposomal suspensions for parenteral administration may be encapsulated with a variety of polymers, sugars, and chelating agents, to yield stable solid liposomal preparations or granules. Polymers for encapsulation may include cross-linked polymers, non-cross-linked polymers, or polymers dispersed within the crystalline structure of sugar starches or protein molecules. Granules may be further processed to yield sublingual films, suppositories, dispersible powder, tablets, gel capsules, or the like.

Compositions for parenteral injection may comprise pharmaceutically acceptable sterile aqueous or non-aqueous solutions, dispersions, suspensions or emulsions as well as sterile powders for reconstitution into sterile injectable solutions or dispersions prior to use. Examples of suitable aqueous and non-aqueous carriers, diluents, solvents or vehicles include, but are not limited to, water, ethanol, polyols, such as glycerol, propylene glycol, polyethylene glycol, and the like, carboxymethyl-cellulose and suitable mixtures thereof, vegetable oils, such as olive oil, and injectable organic esters, such as ethyl oleate. Proper fluidity can be maintained, for example, by the use of coating materials such as lecithin, by the maintenance of the required particle size in the case of dispersions, and by the use of surfactants. The disclosed pharmaceutical compositions for parenteral administration may also contain adjuvants such as, but not limited to, preservatives, wetting agents, emulsifying agents, and dispersing agents, isotonic agents, such as sugars, sodium chloride, and the like, and agents that delay absorption, such as aluminum monostearate and gelatin.

Injectable depot forms may be made by forming microcapsule matrices of the disclosed small molecule inhibitors in biodegradable polymers, such as polylactide-polyglycolide, poly(orthoesters) and poly(anhydrides). Depot injectable formulations may also be prepared by entrapping the disclosed small molecule inhibitors in liposomes or microemulsions compatible with body tissues. Injectable formulations may be sterilized, for example, by filtration through a bacterial-retaining filter, or by incorporating sterilizing agents in the form of sterile solid compositions which can be dissolved or dispersed in sterile water or other sterile injectable medium just prior to use.

Various additives, known to those skilled in the art, may be included in transdermal formulations. Examples of additives include, but are not limited to, solubilizers, skin permeation enhancers, preservatives, such as anti-oxidants, moisturizers, gelling agents, buffering agents, surfactants, emulsifiers, emollients, thickening agents, stabilizers, humectants, dispersing agents and pharmaceutical carriers. Examples of moisturizers include, but are not limited to, jojoba oil and evening primrose oil. Suitable skin permeation enhancers include, but are not limited to, lower alkanols, such as methanol ethanol and 2-propanol; alkyl methyl sulfoxides, such as dimethylsulfoxide (DMSO), decylmethylsulfoxide (C10 MSO) and tetradecylmethyl sulfoxide; pyrrolidones, urea; N,N-diethyl-m-toluamide; C2-C6 alkanediols; dimethyl formamide (DMF), N,N-dimethylacetamide (DMA) and tetrahydrofurfuryl alcohol. Examples of solubilizers include, but are not limited to, hydrophilic ethers, such as diethylene glycol monoethyl ether and diethylene glycol monoethyl ether oleate; polyoxy 35 castor oil, polyoxy 40 hydrogenated castor oil, polyethylene glycol (PEG), and polyethylene glycol derivatives, such as PEG-8 caprylic/capric glycerides; alkyl methyl sulfoxides, such as DMSO; pyrrolidones, DMA, and mixtures thereof.

Prevention and/or treatment of infections can be achieved by the inclusion of antibiotics, as well as various antibacterial and antifungal agents, for example, paraben, chlorobutanol, phenol sorbic acid, and the like, in the disclosed pharmaceutical compositions.

The disclosed pharmaceutical compositions may contain one or more pharmaceutically acceptable excipients, diluents, adjuvants, stabilizers, emulsifiers, preservatives, colorants, buffers, flavor-imparting agents, bacteriostats, fungistats, emollients, plasticizers, permeation enhancers, antioxidants, pigments, lubricants, preservatives, wetting agents, salts, and any mixture thereof, and pharmaceutically acceptable carriers suitable for oral, mucosal, submucosal, enteral, parenteral, intravenous or transdermal administration.

The disclosed pharmaceutical compositions may further comprise one or more of a chemotherapeutic agent, an immunosuppressive agent, an immuno-stimulatory agent, an anti pyretic agent, a cytotoxic agent, a nucleolytic compound, a radioactive isotope, a receptor, a pro-drug activating enzyme, an anti-inflammatory agent, an antibiotic, a protease inhibitor, a growth factor, an osteo-inductive factor, an antibacterial agent or an antifungal agent.

The pharmaceutical compositions provided herein, when administered to a subject, may treat, control, manage or prevent progressive neurological diseases such as, but not limited to, Alzheimer's disease (AD), Parkinson's disease (PD), amyotrophic lateral sclerosis (ALS), multiple sclerosis, Huntington's disease and multiple system atrophy. The subject may be an animal or a human subject.

Methods of Detecting, Preventing, Treating, Controlling or Managing a Progressive Neurological Disease Also provided herein are methods of detecting, preventing, treating, controlling or managing a progressive neurodegenerative disease in subjects that are in need of prophylactic treatment or a cure. Progressive neurodegenerative diseases that may be detected, treated, controlled, managed or prevented by the disclosed methods include, but are not limited to, Alzheimer's disease, Parkinson's disease, Amyotrophic Lateral Sclerosis, multiple sclerosis, Huntington's disease and multiple system atrophy.

The disclosed methods comprise the steps of (a) detecting expression of astrotactin (ASTN1) in a subject's blood monocytes; and (b) administering to the subject a therapeutically effective amount of the antibodies or fragments thereof that are provided herein.

The disclosed methods may comprise administering the antibody or fragment thereof in form of a stable liquid aqueous pharmaceutical formulation in combination with a tonicity agent, a surfactant, and a buffer. The disclosed pharmaceutical formulations may further contain one or more pharmaceutically acceptable excipients, diluents, adjuvants, stabilizers, emulsifiers, preservatives, colorants, buffers, flavor-imparting agents or pharmaceutically acceptable carriers suitable for enteral, parenteral, or intravenous administration.

The disclosed methods may further comprise administering one or more of a chemotherapeutic agent, an immunosuppressive agent, an immuno-stimulatory agent, an anti pyretic agent, a cytotoxic agent, a nucleolytic compound, a radioactive isotope, a receptor, a pro-drug activating enzyme, an anti-inflammatory agent, an antibiotic, a protease inhibitor, a growth factor, an osteo-inductive factor, an antibacterial agent or an antifungal agent to the subject. Such active agents may be administered prior to, simultaneously with, or after administering the disclosed antibodies or fragments thereof.

In some examples, the disclosed methods may further comprise a step of detecting abnormal elevated expression of one or more cytokine, or one or more signaling pathway in the subject. The cytokine may be one or more of IL-1b, IL-6 or TNF. The signaling pathway is one or more of Janus tyrosine Kinase (JAK) pathway, or Signal Transducer and Activator of Transcription (STAT) pathway.

Thus, the methods disclosed herein provide effective detection, treatment, prevention, control and/or management of progressive neurodegenerative diseases.

Diagnosis with Machine Learning Classifier

The disclosed methods may comprise the use of a machine learning classifier to determine whether a subject is a good candidate for treatment. Machine learning classifiers include, but are not limited to, a random forest classifier.

The disclosed method may comprise collecting a biological sample from a subject; performing high-throughput RNA sequencing, such as Illumina sequencing, on the sample to sequence the RNA transcripts present in the cells of the sample; and matching at least some of the RNA reads output obtained from the high-throughput sequencing to their corresponding RNA transcripts in an RNA transcript dictionary.

The disclosed method may further comprise classifying some RNA reads that do not match an RNA transcript in the RNA transcript dictionary into a gene or gene family by one or more machine learning classifiers, such as neural networks, which have been trained to classify RNA reads to a gene or gene transcript based on training examples.

Further steps in the disclosed method may include quantifying the RNA transcripts. A first plurality of RNA reads that matched to an RNA transcript may be quantified by matching to RNA scaffolds that may be partially filled in according to matches with RNA reads and counted. A second plurality of RNA reads that were classified by the one or more machine learning classifiers may be quantified by assembling the RNA reads together by identifying RNA reads that map to the same gene or gene family and have overlapping sequence on an end. The assembled RNA transcripts may be counted. As a result an RNA transcriptome may be determined including the identity and quantity of RNA transcripts of the subject in the sample.

The RNA transcriptome may be input to a disease prediction machine learning classifier, such as a random forest classifier, that is trained to predict whether a subject has a disease or will have variation in treatment response. Variation in treatment response may include a patient reacting poorly to a standard treatment for a disease either by having an incomplete response to therapy or by causing new disease features to emerge. The disease prediction machine learning classifier may predict based on the RNA transcriptome whether the subject's cells, such as blood monocytes, are expressing ASTN1 and the antibodies disclosed herein should be administered.

The disclosed method may include administering treatment to the subject based on the output prediction of the disease prediction machine learning classifier.

The disclosed method may include, when the disease prediction machine learning classifier detects elevated activity of ASTN1, administering an effective dose of a pharmaceutical composition to inhibit ASTN1 activity and, when the disease prediction machine learning classifier does not detect elevated activity of ASTN1, not administering the effective dose. Further details of this method of diagnosis are described in U.S. Provisional Patent Application No. [62/719,614], filed on Aug. 18, 2018, which is hereby incorporated by reference in its entirety.

EXAMPLES

Example 1: Involvement of ASTN1 in Huntington's Disease (HD)

The sequences of RNA transcriptomes obtained from monocytes isolated from the peripheral blood of 30 manifest HD subjects and 33 control subjects with no HD (Accession Number: PRJEB12995) were analyzed by random forest analysis to identify the differences between HD subjects and healthy controls. The Random Forest analysis, which was trained on Huntington disease (1) versus healthy controls (0), identified the presence of ASTN1 in blood monocytes as a major factor associated with HD.

Example 2: Antibodies, Antibody Fragments and Antibody-Drug Conjugates Binding ASTN1

ASTN1 is a membrane-spanning protein, characterized by the presence of two transmembrane helices, a cytosolic domain and an extracellular region (ECD2), which contains a small N-terminal domain and a large C-terminal domain. The ECD2 region, which faces outward from the cell to the blood fluid, allows cells expressing ASTN1, such as blood monocytes, to interact with other cells and proteins.

In designing the antibodies, two strategies were developed. In a first strategy, the aim was to prevent the migration of blood monocytes expressing ASTN1 into the CNS, by blocking their interaction with glial cells in the brain and their response to chemotactic gradient. This would lead to a reduction in the level of inflammation in the brain brought about by proinflammatory monocytes.

In a second approach, the aim was to neutralize blood monocytes expressing ASTN1 with monoclonal antibodies that bind the ECD2 of ASTN1 in the blood.

Monoclonal antibodies and monoclonal antibody-drug conjugates against epitopes on the extracellular domain 2 (ECD2) of the ASTN1 protein were therefore designed and built. Single chain variable fragment (scFv) proteins were designed using in-house proprietary software. DNA sequences were translated into DNA sequences using codon optimization. Gene sequences were codon-optimized for *E. coli* production, synthesized and cloned into the pET20b(+) vector using the GenScript gene synthesis and cloning services. Ten different variants of scFv constructs were transformed into Rosetta Gami *E. coli* strain according to the manufacturer's recommendations. The plasmid-carrying *E. coli* cells were grown at 30° C. and induced with 0.2 mM IPTG for 5 hours at 30° C. Expressed scFVs were extracted according to the in-house proprietary SOP, and purified using the NiNTA method. Purified proteins were stored at −80° C.

Different Monoclonal Antibodies were Built:

In some embodiment, the monoclonal antibodies or fragments thereof comprised a heavy chain VR and a light chain VR, wherein the heavy chain VR comprised an amino acid sequence of SEQ ID NO: 1, and wherein the light chain VR comprised an amino acid sequence of SEQ ID NO: 2.

In some embodiment, the disclosed antibodies or fragments thereof comprised a heavy chain VR and a light chain VR, wherein the heavy chain VR comprised an amino acid sequence of SEQ ID NO: 3, and wherein the light chain VR comprised an amino acid sequence of SEQ ID NO: 4.

These monoclonal antibodies or fragments thereof were able to bind one or more residues in ASTN1 extracellular domain 1205-1208 region including, but not limited to, one or more of Gln1205, His1206, Tyr1207 and Glu1208.

In other embodiments, the monoclonal antibodies or fragments thereof comprised a heavy chain VR and a light chain VR, wherein the heavy chain VR comprised heavy chain CDRs comprising anyone of SEQ ID NO: 5, SEQ ID NO: 6, or SEQ ID NO: 7, and wherein the light chain VR comprised light chain CDRs comprising anyone of SEQ ID NO: 8, SEQ ID NO: 9, or SEQ ID NO: 10.

In yet other embodiments, the monoclonal antibodies or fragments thereof comprised a heavy chain VR and a light chain VR, wherein the heavy chain VR comprised heavy chain CDRs comprising anyone of SEQ ID NO: 11, SEQ ID NO: 12, or SEQ ID NO: 13, and wherein the light chain VR comprised light chain CDRs comprising anyone of SEQ ID NO: 14, SEQ ID NO: 15, or SEQ ID NO: 16.

These monoclonal antibodies and fragments thereof bind ASTN1 at one or more residues, which include: Phe757, Arg758, Gln759, Asn760, Asn761, Phe762, Ala763, Arg764, Gly765, Leu766, Asp767, Gln768, Gln769, Val775, Val776, Ala777, Thr778, Val808, Arg888, Arg911, Lys931, His932, Ala935, Thr1073, Asp1074, Arg1075, Met1076, Asp1077, His1078, Ser1079, Lys1080, Val1081, Glu1082, Thr1083, Thr1085, Leu1087, Asp1092, Ser1095, Gly1096, Ala1097, Lys1098, Ser1099, Pro1100, Cys1101, Ala1102, Ile1119, Glu1123, Pro1124, Lys1160, Glu1163, Ile1164, Lys1167, Asn1168, Thr1176, Gln1182, Thr1183, Tyr1185, Asn1186, Leu1189, Asp1190, Leu1191, Gly1192, Ser1193, Tyr1201, Gln1205, His1206, Glu1208, Ser1209, Glu1212, Trp1215, Glu1218, Pro1223, Arg1224, Gly1227, Leu1230, Ser1231, Gln1232, Gly1234, Gln1235, Gln1245, Glu1246, Pro1247, Tyr1296, Gly1297, Asp1298, Ser1299, and Lys1300.

In developing antibody-drug conjugates (ADCs), a cytotoxin drug is coupled to the disclosed antibody or antibody fragment that specifically targets ASTN1, such that the disclosed antibody or fragment thereof may detect ASTN1 and attach to the surface of blood monocytes carrying ASTN1. The biochemical reaction between the antibody and ASTN1 triggers a signal in the blood monocytes, which then absorb or internalize the antibody together with the cytotoxin drug. Once the ADC is internalized, the cytotoxic drug is released and kills the blood monocytes carrying ASTN1.

Example 3: Functional Validation of the Disclosed Antibodies

Different variants of the disclosed antibodies and antibody fragments (ScFv) were designed, synthesized, cloned, codon-optimized for *Escherichia coli* expression, expressed in *E. coli*, extracted and only partially purified (60-70% pure). The following antibodies and antibody fragments were designed, synthesized, cloned and purified, and tested for their ability to bind ASTN1; ScFv3: full-length antibody in the presence of ASTN1; ScFv7: antibody fragment in the presence of ASTN1; anti-His: synthetic oligo peptide consisting of six histidine residues used as positive control in the presence of ASTN1; ScFv4: antibody fragment in the presence of ASTN1; no antigen-ScFv3: negative control (full-length antibody in the absence of ASTN1); no antigen-ScFv7: negative control (antibody fragment in the absence of ASTN1). The interaction of the disclosed antibodies and antibody fragments was determined by ELISA and measured by optical density at 450 nm. ASTN1 was diluted to a final concentration of 40 ng/µl in PBS/1 mM $CaCl_2$, and 35 µL of the solution per well was coated on the wells of a PVC microtiter plate (96 wells). Uncoated wells served as negative control. The disclosed antibodies, antibody fragments and anti-His antibody were diluted to desired concentrations using blocking buffer as the diluent with a final volume of 50 µl and dispensed into the assigned wells. Each sample was run in several duplicates.

The results, shown in FIG. 1, demonstrate that the ScFv3 full-length antibody at a concentration of 250 nM binds ASTN1 at a detectable level, as compared to the positive control. Antibody fragments ScFv7 and ScFv4 were not effective. As expected, the negative controls showed no binding in the absence of ASTN1.

Figure 2:
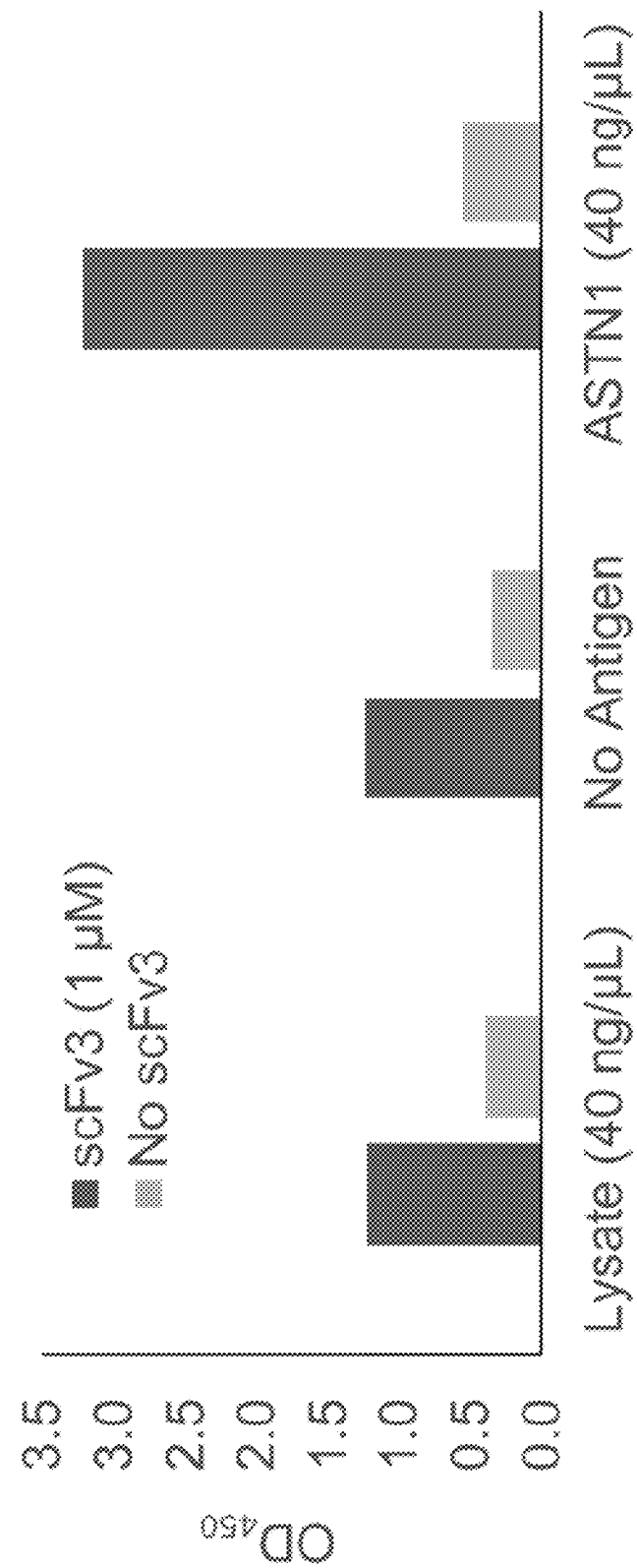
FIG. 2 shows that the scFv3 antibody does not bind to proteins in a crude human lysate, and does not show any activity in the absence of antigen. However, the scFv3 antibody strongly binds ASTN1 recombinant protein when present in a concentration of 40 ng/ml. These results indicate that the scFv3 antibody is highly specific for ASTN1.

Example 4: Functional Validation of the scFv3 Antibody and of the scFv5 Antibody To further validate the scFv3 antibody, scFv3 antibody binding was assessed in a crude humane lysate, in the absence of antigen, and in the presence of ASTN1. As shown in FIG. 2, the scFv3 antibody does not bind to proteins in a crude human lysate, and does not show any activity in the absence of antigen. However, the scFv3 antibody strongly binds ASTN1 recombinant protein when present in a concentration of 40 ng/ml. These results indicate that the scFv3 antibody is highly specific for ASTN1.

Figure 3:
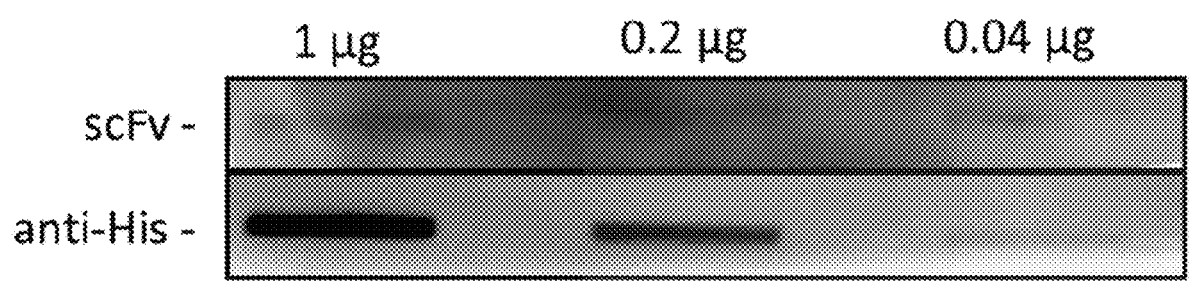
FIG. 3 shows the results of ASTN1 Western blot analysis. In particular, the results show that the scFv3 antibody does not bind denatured ASTN1 in a western blot system when applied in an amount of 1 μg, 0.2 μg, or 0.04 μg. These results indicate that the scFv3 antibody binds ASTN1 only in its original three-dimensional form.

To determine whether protein denaturation affects antibody binding, ASTN1 was denaturated by SDS, and scFv3 antibody binding was assessed by western blot analysis. As shown in FIG. 3, the scFv3 antibody does not bind denaturated ASTN1 in a western blot system when applied in an amount of 1 µg, 0.2 µg, or 0.04 µg. These results indicate that the scFv3 antibody binds ASTN1 only in its original three-dimensional form.

Figure 6:
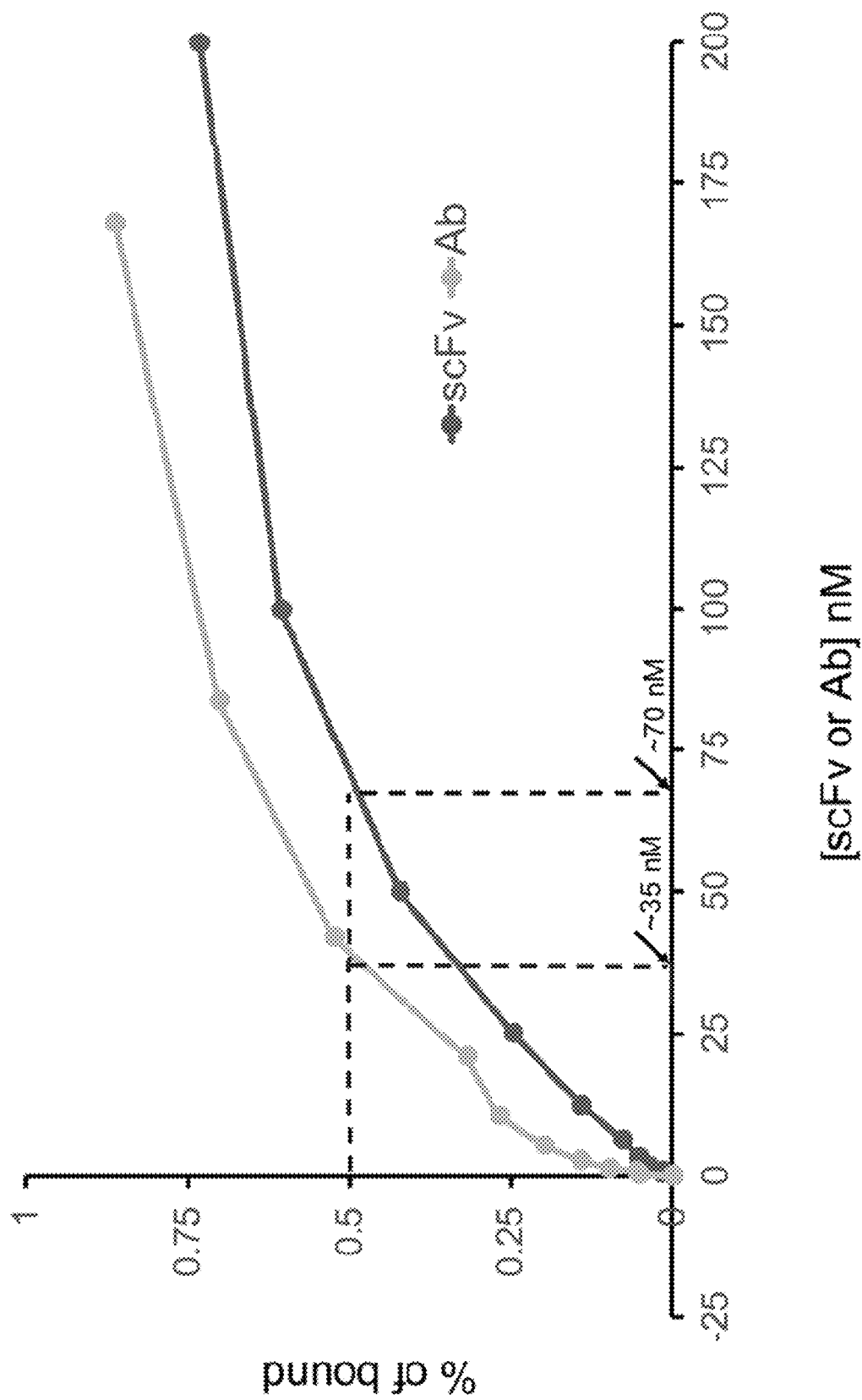
FIG. 6 shows the affinity of the scFv3 antibody for ASTN1 in its natural form and when placed in a human IgG1 construct. The scFv3 antibody in its natural form binds ASTN1 at 70 nM, and the scFv3 antibody in the human IgG1 construct binds ASTN1 at 35 nM.

To further study the affinity of the scFv3 antibody for ASTN1, binding of the scFv3 antibody to ASTN1 was assessed for the scFv3 antibody in its natural form and when placed in a human IgG1 construct. As shown in FIG. 6, the scFv3 antibody in its natural form binds ASTN1 at 70 nM, and the scFv3 antibody in the human IgG1 construct binds ASTN1 at 35 nM. These results indicate that the affinity of the scFv3 antibody for ASTN1 increases when the antibody is constructed in human IgG1.

Figure 4:
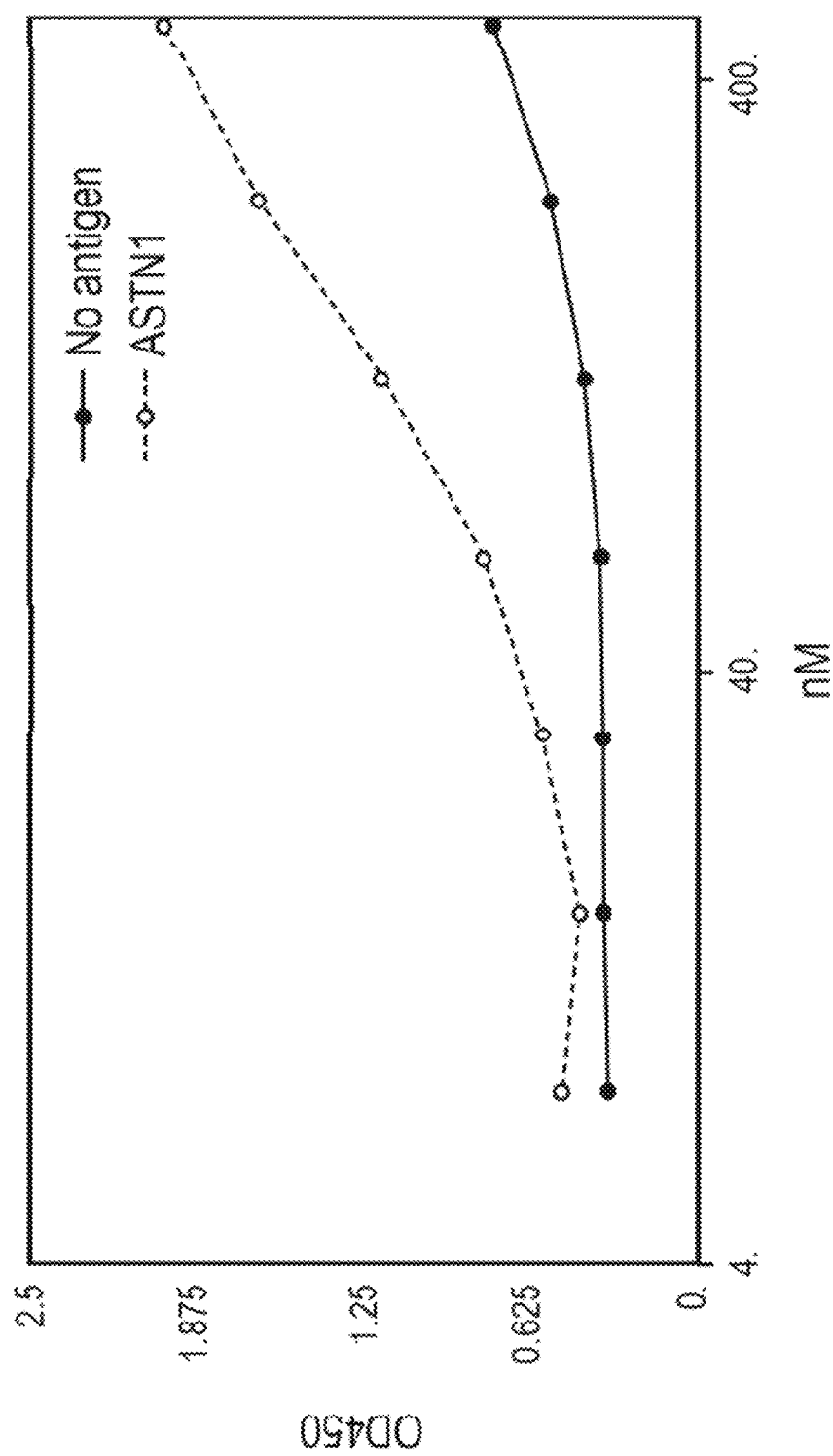
FIG. 4 is a graph showing that the scFv5 antibody binds ASTN1 at 100 nM.

The level of affinity of the scFv5 antibody for ASTN1 was also assessed. As shown in FIG. 4, the scFv5 antibody binds ASTN1 at 100 nM.

Figure 5:
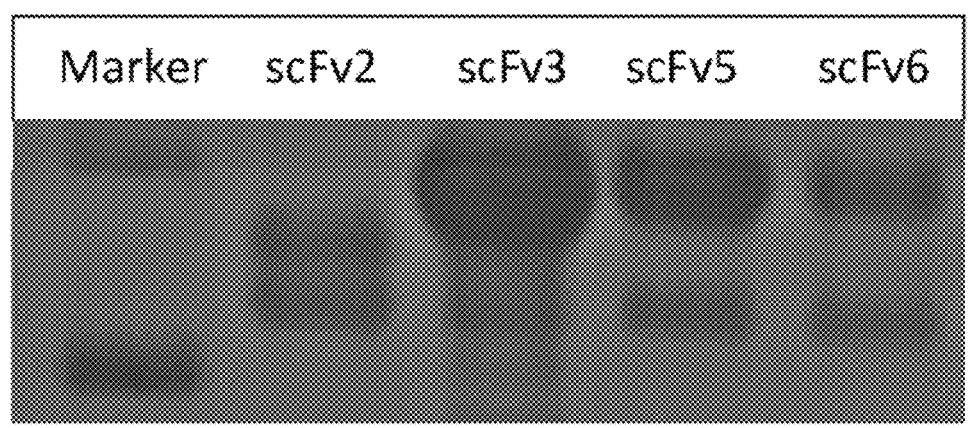
FIG. 5 shows that the binding region of the scFv3 antibody and the binding region of the scFv5 antibody are readily purified and recovered from their preparations.

The disclosed antibodies can be easily recovered and purified. As shown in FIG. 5, the binding region of the scFv3 antibody and the binding region of the scFv5 antibody are readily purified and recovered from their gel preparations.

Figure 7A:
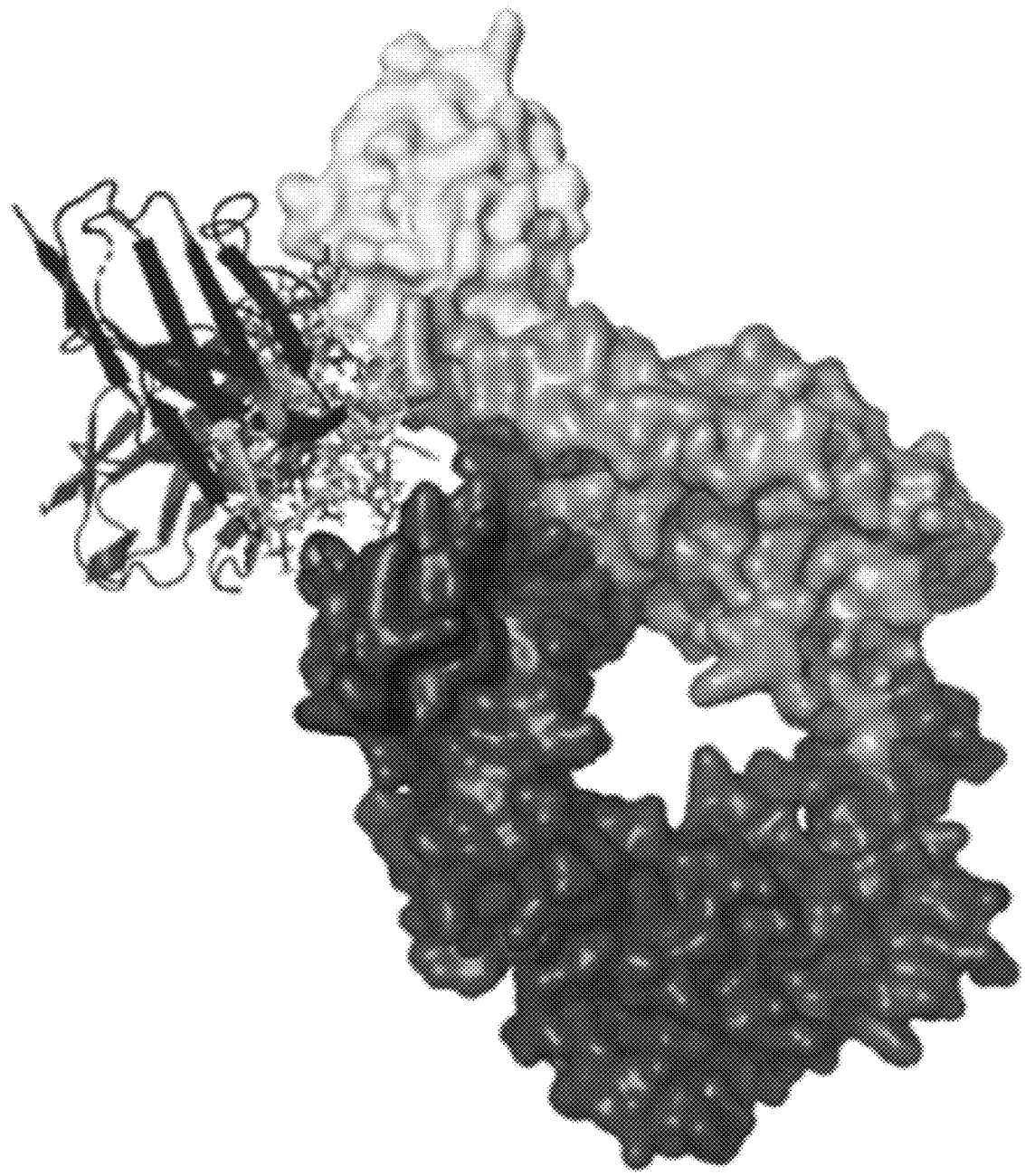
FIG. 7A shows the structure of the ASTN1 protein, the structure of the scFv3 antibody, and the putative antibody for the scFv3 antibody, that were generated by molecular modeling.
Figure 7B:
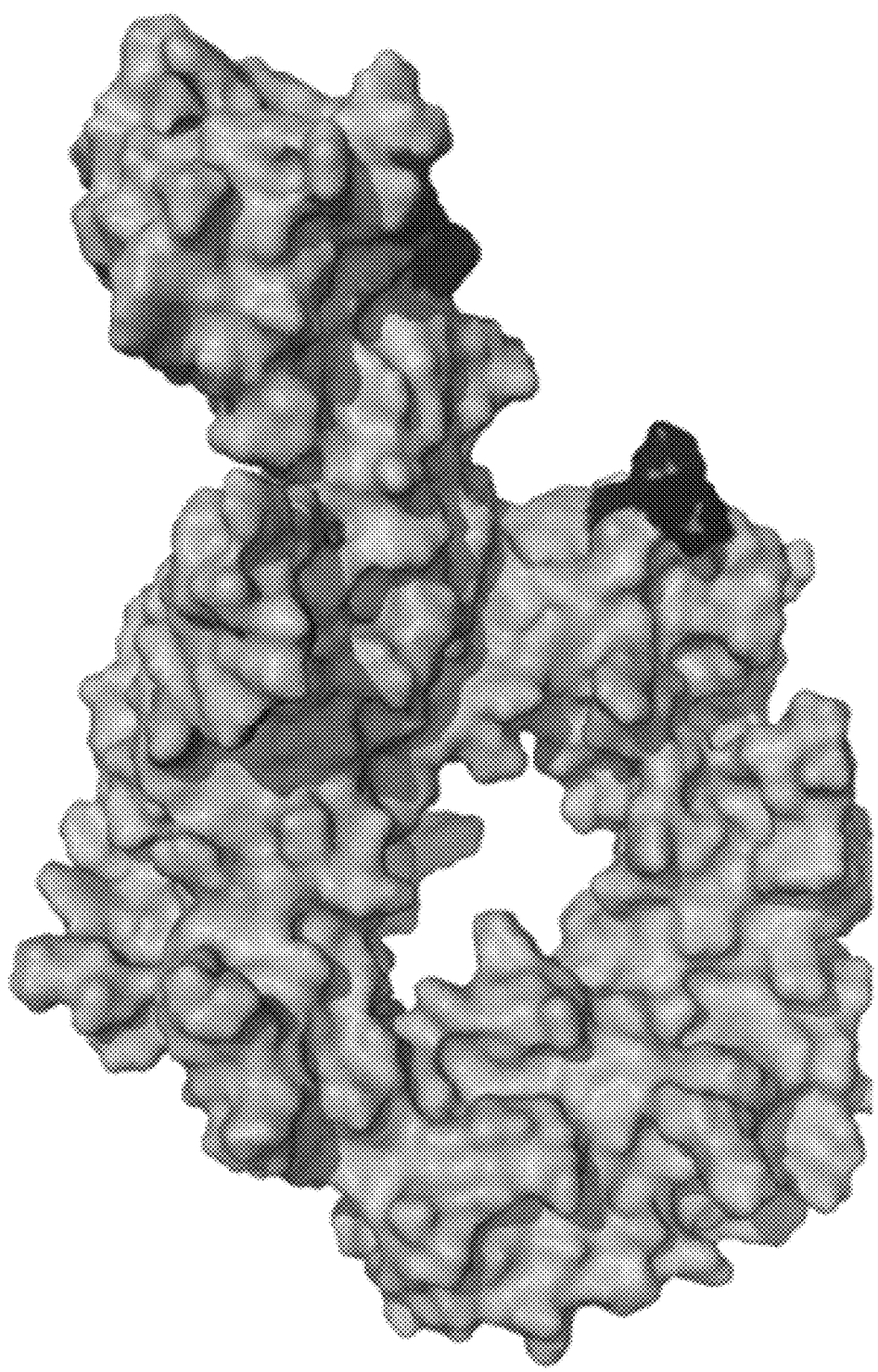
FIG. 7B shows point mutations that were introduced into regions of the ASTN1 sequence for epitope validation.

Example 5: The Binding Epitope for the scFv3 Antibody Comprises the 1205-1208 Region of ASTN1 Extracellular Domain Molecular modeling was used to determine the structure of the ASTN1 protein and the structure of the scFv3 antibody. FIG. 7A shows the structure of the ASTN1 protein, the structure of the scFv3 antibody, and the putative epitope for the scFv3 antibody, that were generated by molecular modeling. FIG. 7B shows point mutations that were introduced into regions of the ASTN1 sequence for epitope validation.

Figure 8A:
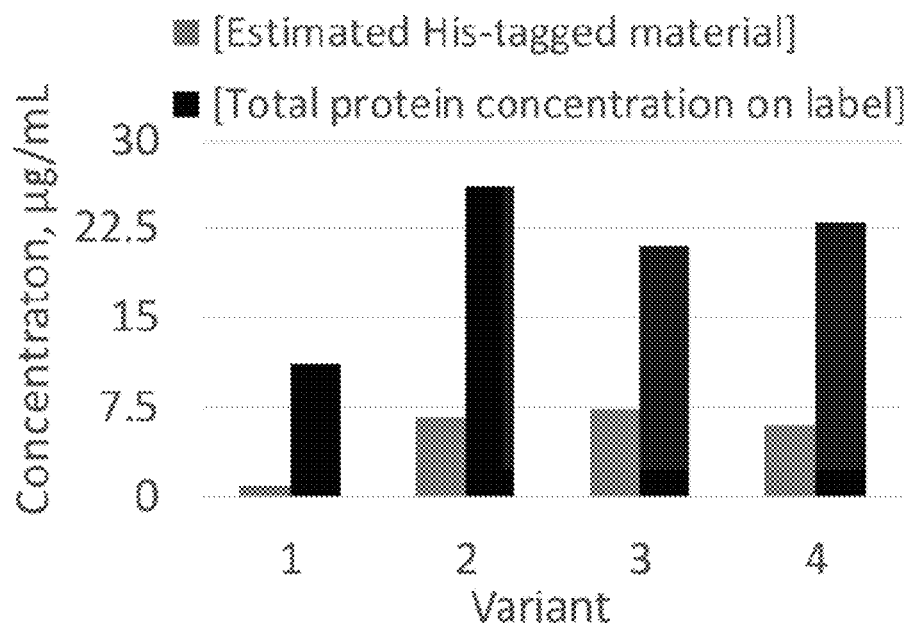
FIG. 8A is a graph showing the amounts of purified ASTN1 variants containing desired point mutations that were generated by GenScript and tested for antibody binding. For each variant, the column on the left indicates the estimated His-tagged concentration of the ASTN1 protein, and the column on the right indicates the total protein concentration. The estimated His-tagged concentrations were used for assessing antibody binding.
Figure 8B:
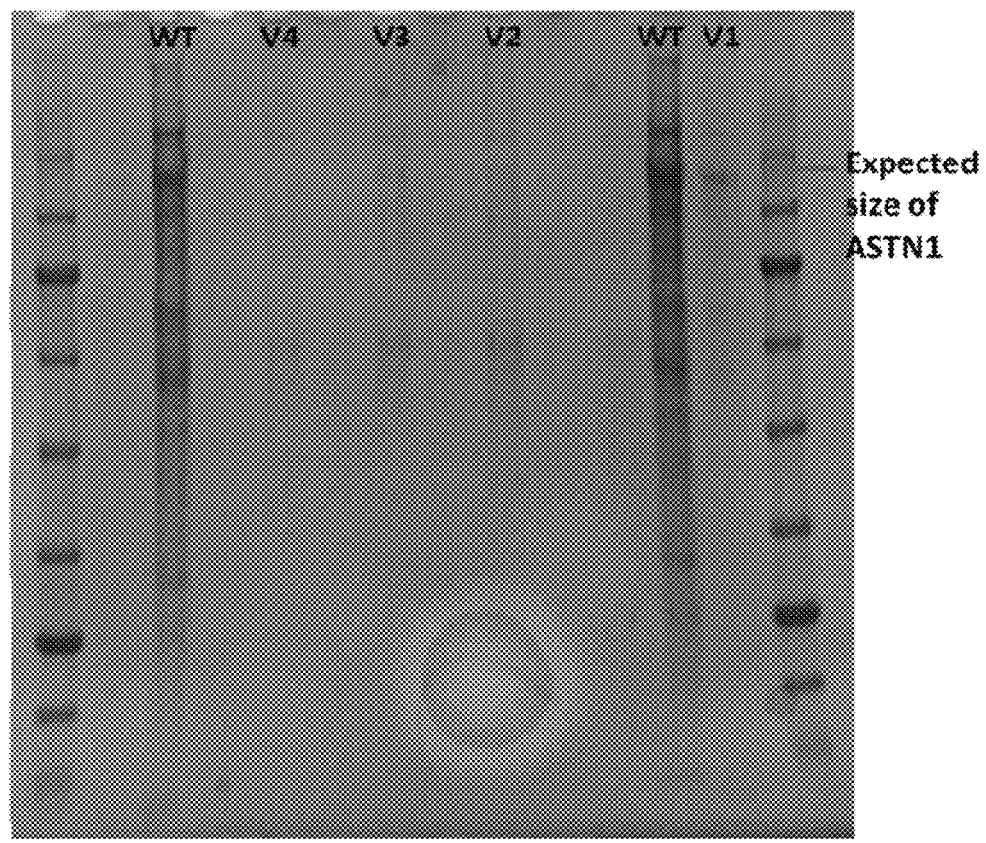
FIG. 8B shows that expression of ASTN1 protein variants comprising point mutations strongly declines as compared to the expression of wild-type ASTN1 protein. These results indicate that folding caused by mutations decreases ASTN1 stability.

To determine the epitope region on the ASTN1 protein, ASTN1 variants containing desired point mutations were tested for antibody binding. FIG. 8A is a graph showing the amounts of purified ASTN1 variants containing desired point mutations that were generated by GenScript and tested for antibody binding. For each variant, the column on the left indicates the estimated His-tagged concentration of the ASTN1 protein, and the column on the right indicates the total protein concentration. The estimated His-tagged concentrations were used for assessing antibody binding. As shown in FIG. 8B, expression of ASTN1 protein variants comprising point mutations strongly declines as compared to the expression of wild-type ASTN1 protein. These results indicate that protein unfolding caused by mutations decreases ASTN1 stability.

Figure 9:
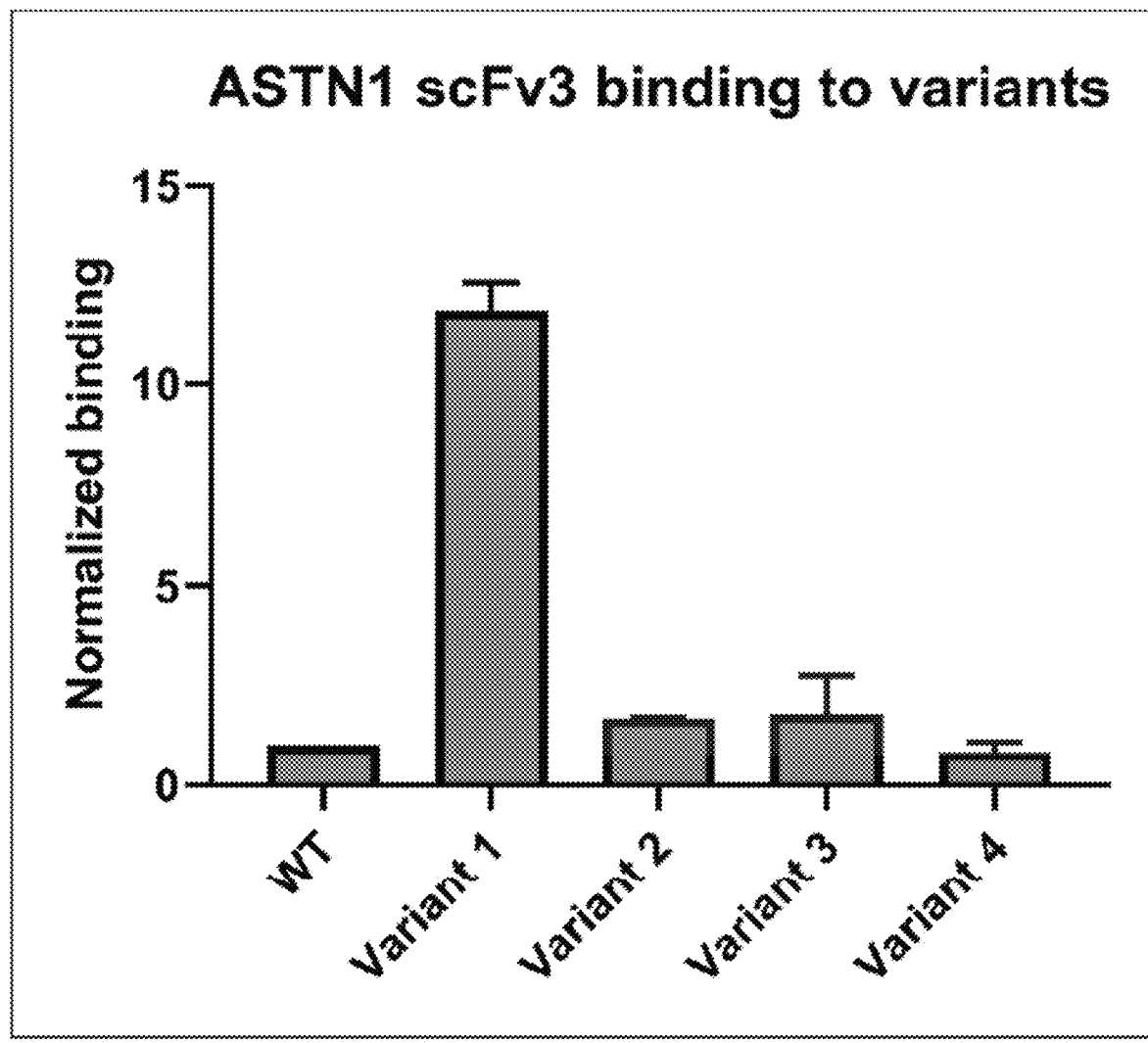
FIG. 9 shows that binding of the scFv3 antibody to ASTN1 protein variants comprising point mutations in the 1205-1208 region of the extracellular domain of the protein increases as compared to binding of the scFv3 antibody to wild-type ASTN1 protein. Variant 1 showing greatest increase comprises Q1205K, H1206A, Y1207A and E2108R mutations in the 1205-1208 region of ASTN1 extracellular domain. These results indicate that the binding epitope for the scFv3 antibody comprises the 1205-1208 region of ASTN1 extracellular domain.
Figure 10:
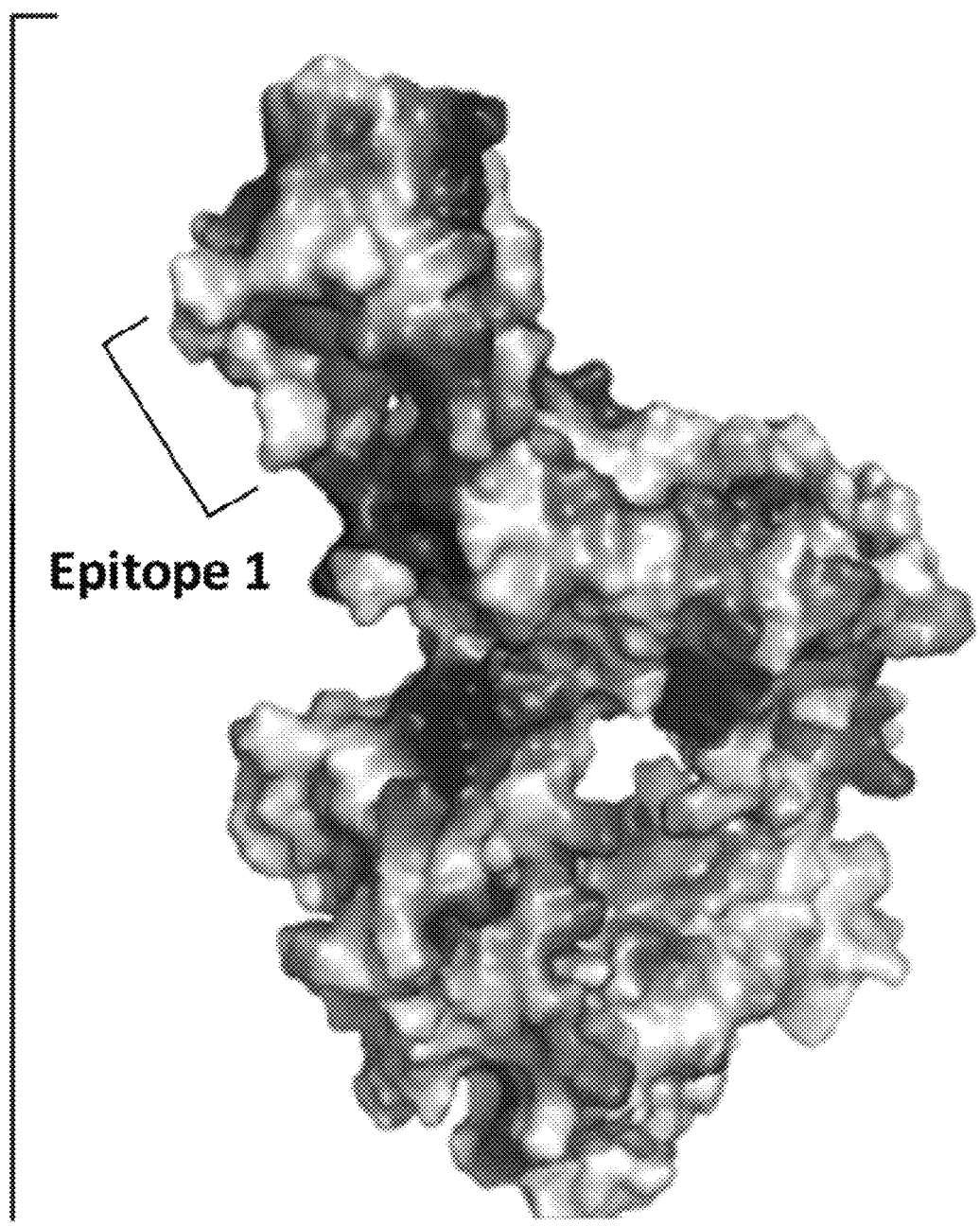
FIG. 10 shows the structure of the ASTN1 protein variant comprising the Q1205K, H1206A, Y1207A and E2108R mutations in the 1205-1208 region of ASTN1 extracellular domain.

As shown in FIG. 9, binding of the scFv3 antibody to ASTN1 protein variants comprising point mutations in the 1205-1208 region of the extracellular domain of the protein strongly increased as compared to binding of the scFv3 antibody to wild-type ASTN1 protein. Variant 1, which showed the greatest increase in binding, comprised Q1205K, H1206A, Y1207A and E2108R mutations in the 1205-1208 region of ASTN1 extracellular domain. FIG. 10 shows the structure of the ASTN1 protein Variant 1, which comprises the Q1205K, H1206A, Y1207A and E2108R mutations in the 1205-1208 region of ASTN1 extracellular domain.

These results indicate that the binding epitope for the scFv3 antibody comprises the 1205-1208 region of ASTN1 extracellular domain.

Example 6: Prophylactic Detection of Blood Monocytes Carrying ASTN1 in Subjects with a Family History of Progressive Neurodegenerative Disease Blood samples from healthy individuals with a family history of progressive neurodegenerative disease and control healthy individuals are collected and blood monocytes are isolated. The isolated blood monocytes from the two groups of individuals are then exposed to the disclosed monoclonal antibody-drug conjugates for detection of blood monocytes carrying ASTN1.

No blood monocytes carrying ASTN1 are detected in the control group. Blood monocytes carrying ASTN1 are detected in various concentrations in individuals with a family history of progressive neurodegenerative disease. These individuals are assessed for candidacy for treatment with the disclosed anti-ASTN1 pharmaceutical formulations.

Example 7: Efficacy of the Disclosed Antibodies in Subjects with Moderate-to-Severe Huntington Disease The efficacy of the disclosed pharmaceutical compositions compared to placebo is assessed for treatment of signs and symptoms in subjects with moderate-to-severe Huntington disease exhibiting one or more symptoms of the disease.

The disclosed antibodies are formulated as pharmaceutical compositions and administered i.v. in two initial doses at days 1 and 15. This experimental regimen is compared to a same regimen where a pharmaceutical composition containing placebo is administered in place of the disclosed antibodies. 10 subjects are included in each of the two groups. Subjects are monitored for disease activity and symptoms, such as depression, forgetfulness, impaired judgment, unsteady gait, involuntary movements, slurred speech, difficulty in swallowing and significant weight loss, over a period of one year.

At the end of the one-year period, subjects treated with the disclosed antibodies show a significant improvement of symptoms and indicators of HD over the control.

It should be recognized that illustrated embodiments are only examples of the disclosed product and methods and should not be considered a limitation on the scope of the invention. Rather, the scope of the invention is defined by the following claims. We therefore claim as our invention all that comes within the scope and spirit of these claims.

What is claimed is:

1. An antibody or fragment thereof, comprising a heavy chain variable region (VR) and a light chain VR, wherein the heavy chain VR comprises an amino acid sequence of SEQ ID NO: 1, and wherein the light chain VR comprises an amino acid sequence of SEQ ID NO: 2.

2. The antibody or fragment thereof of claim 1, wherein the antibody or fragment thereof binds one or more residues in the astrotactin (ASTN1) extracellular domain 1205-1208 region, and wherein the one or more residues comprise one or more of Gln1205, His1206, Tyr1207 and Glu1208.

3. A stable liquid aqueous pharmaceutical formulation, wherein the liquid aqueous pharmaceutical formulation comprises the antibody or fragment thereof of claim 1, a tonicity agent, a surfactant, and a buffer, and wherein the liquid aqueous pharmaceutical formulation optionally further comprises one or more pharmaceutically acceptable excipients, diluents, adjuvants, stabilizers, emulsifiers, preservatives, colorants, buffers, flavor-imparting agents or pharmaceutically acceptable carriers suitable for enteral, parenteral, or intravenous administration.

4. The stable liquid aqueous pharmaceutical formulation of claim 3, wherein the liquid aqueous pharmaceutical formulation further comprises one or more of a chemotherapeutic agent, an immunosuppressive agent, an immunostimulatory agent, an anti-pyretic agent, a cytotoxic agent, a nucleolytic compound, a radioactive isotope, a receptor, a pro-drug activating enzyme, an anti-inflammatory agent, an antibiotic, a protease inhibitor, a growth factor, an osteoinductive factor, an antibacterial agent or an antifungal agent.

5. An antibody or fragment thereof, comprising a heavy chain variable region (VR) and a light chain VR, wherein the heavy chain VR comprises an amino acid sequence of SEQ ID NO: 3, and wherein the light chain VR comprises an amino acid sequence of SEQ ID NO: 4.

6. A stable liquid aqueous pharmaceutical formulation, wherein the liquid aqueous pharmaceutical formulation comprises the antibody or fragment thereof of claim 5, a tonicity agent, a surfactant, and a buffer, and wherein the liquid aqueous pharmaceutical formulation optionally further comprises one or more pharmaceutically acceptable excipients, diluents, adjuvants, stabilizers, emulsifiers, preservatives, colorants, buffers, flavor-imparting agents or pharmaceutically acceptable carriers suitable for enteral, parenteral, or intravenous administration.

7. The stable liquid aqueous pharmaceutical formulation of claim 6, wherein the liquid aqueous pharmaceutical formulation further comprises one or more of a chemotherapeutic agent, an immunosuppressive agent, an immunostimulatory agent, an anti-pyretic agent, a cytotoxic agent, a nucleolytic compound, a radioactive isotope, a receptor, a pro-drug activating enzyme, an anti-inflammatory agent, an antibiotic, a protease inhibitor, a growth factor, an osteoinductive factor, an antibacterial agent or an antifungal agent.

* * * * *